United States Patent
Dobrinsky

(10) Patent No.: US 11,608,279 B2
(45) Date of Patent: Mar. 21, 2023

(54) ULTRAVIOLET IRRADIATION OF FLUIDS

(71) Applicant: Sensor Electronic Technology, Inc., Columbia, SC (US)

(72) Inventor: Alexander Dobrinsky, Silver Spring, MD (US)

(73) Assignee: Sensor Electronic Technology, Inc., Columbia, SC (US)

(*) Notice: Subject to any disclaimer, the term of this patent is extended or adjusted under 35 U.S.C. 154(b) by 452 days.

(21) Appl. No.: 16/288,836

(22) Filed: Feb. 28, 2019

(65) Prior Publication Data

US 2019/0263680 A1   Aug. 29, 2019

Related U.S. Application Data

(60) Provisional application No. 62/636,830, filed on Feb. 28, 2018.

(51) Int. Cl.
| | |
|---|---|
| *C02F 1/32* | (2006.01) |
| *C02F 1/00* | (2006.01) |
| *A61L 2/10* | (2006.01) |
| *A61L 2/24* | (2006.01) |

(52) U.S. Cl.
CPC .............. *C02F 1/325* (2013.01); *A61L 2/10* (2013.01); *A61L 2/24* (2013.01); *C02F 1/003* (2013.01); *A61L 2202/14* (2013.01); *A61L 2202/23* (2013.01); *C02F 2201/326* (2013.01); *C02F 2201/3222* (2013.01); *C02F 2201/3227* (2013.01); *C02F 2201/3228* (2013.01)

(58) Field of Classification Search
CPC .. C02F 1/325; C02F 1/003; C02F 1/32; C02F 1/00; C02F 2201/3222; C02F 2201/3227; C02F 2201/3228; C02F 2201/326; C02F 2307/00; C02F 2307/02; C02F 2307/04; C02F 2307/10; A61L 2/10; A61L 2/24; A61L 2202/14; A61L 2202/23
USPC ....................................................... 210/138
See application file for complete search history.

(56) References Cited

U.S. PATENT DOCUMENTS

| | | | |
|---|---|---|---|
| 7,553,456 B2 | 6/2009 | Gaska et al. | |
| 7,634,996 B2 | 12/2009 | Gaska et al. | |
| 8,128,820 B2 | 3/2012 | Wu | |
| 8,177,966 B2 | 5/2012 | Wu | |
| 8,277,734 B2 | 10/2012 | Koudymov et al. | |
| 8,980,178 B2 | 3/2015 | Gaska et al. | |
| 9,006,680 B2 | 4/2015 | Bettles et al. | |
| 9,034,271 B2 | 5/2015 | Shur et al. | |
| 9,061,082 B2 | 6/2015 | Gaska et al. | |

(Continued)

*Primary Examiner* — Akash K Varma
(74) *Attorney, Agent, or Firm* — LaBatt, LLC

(57) ABSTRACT

Ultraviolet irradiation of liquids for purposes of sterilization, disinfection, cleaning and/or treatment. A liquid collection reservoir can receive an inflow of a liquid. A filtering unit can filter the inflow of liquid received by the liquid collection reservoir. A liquid chamber stores the liquid. Ultraviolet light emitting sources located about the liquid chamber irradiate the liquid in the liquid chamber with ultraviolet light. A control unit, operatively coupled to the ultraviolet light emitting sources, controls the irradiation of the liquid in the liquid chamber with the ultraviolet light emitting sources. The control unit is configured to control an intensity and a duration of the irradiation as a function of time that the liquid is stored in the liquid chamber and the amount of the liquid that is in the liquid chamber.

20 Claims, 7 Drawing Sheets

(56) References Cited

U.S. PATENT DOCUMENTS

| | | |
|---|---|---|
| 9,138,499 B2 | 9/2015 | Bettles et al. |
| 9,179,703 B2 | 11/2015 | Shur et al. |
| 9,517,948 B1 | 12/2016 | Garrett |
| 9,572,903 B2 | 2/2017 | Dobrinsky et al. |
| 9,603,960 B2 | 3/2017 | Dobrinsky et al. |
| 9,687,577 B2 | 6/2017 | Dobrinsky et al. |
| 9,707,307 B2 | 7/2017 | Shur et al. |
| 9,718,706 B2 | 8/2017 | Smetona et al. |
| 9,724,441 B2 | 8/2017 | Shur et al. |
| 9,750,830 B2 | 9/2017 | Shur et al. |
| 9,757,486 B2 | 9/2017 | Dobrinsky et al. |
| 9,795,699 B2 | 10/2017 | Shur et al. |
| 9,801,965 B2 | 10/2017 | Bettles et al. |
| 9,802,840 B2 | 10/2017 | Shturm et al. |
| 9,878,061 B2 | 1/2018 | Shur et al. |
| 9,919,068 B2 | 3/2018 | Shur et al. |
| 9,974,877 B2 | 5/2018 | Bettles et al. |
| 9,981,051 B2 | 5/2018 | Shur et al. |
| 9,987,383 B2 | 6/2018 | Bilenko et al. |
| 9,999,782 B2 | 6/2018 | Shur et al. |
| 10,004,821 B2 | 6/2018 | Dobrinsky et al. |
| 10,040,699 B2 | 8/2018 | Smetona et al. |
| 10,099,944 B2 | 10/2018 | Smetona et al. |
| 2007/0209984 A1* | 9/2007 | Lev .................. C02F 1/325 210/143 |
| 2010/0215552 A1* | 8/2010 | Wu .................. C02F 1/003 422/186.3 |
| 2010/0243582 A1 | 9/2010 | Riedel et al. |
| 2011/0084006 A1* | 4/2011 | Wu .................. C02F 1/003 210/85 |
| 2013/0048545 A1 | 2/2013 | Shatalov et al. |
| 2014/0202962 A1 | 7/2014 | Bilenko et al. |
| 2016/0114186 A1 | 4/2016 | Dobrinsky et al. |
| 2017/0057842 A1 | 3/2017 | Dobrinsky et al. |
| 2017/0100495 A1 | 4/2017 | Shur et al. |
| 2017/0189711 A1 | 7/2017 | Shur et al. |
| 2017/0245527 A1 | 8/2017 | Dobrinsky et al. |
| 2017/0245616 A1 | 8/2017 | Lakios et al. |
| 2017/0281812 A1 | 10/2017 | Dobrinsky et al. |
| 2017/0290934 A1 | 10/2017 | Dobrinsky et al. |
| 2017/0368215 A1 | 12/2017 | Shatalov et al. |
| 2018/0028700 A1 | 2/2018 | Dobrinsky et al. |
| 2018/0092308 A1 | 4/2018 | Dobrinsky et al. |
| 2018/0104368 A1 | 4/2018 | Dobrinsky et al. |
| 2018/0117194 A1 | 5/2018 | Dobrinsky et al. |
| 2018/0185529 A1 | 7/2018 | Shur et al. |
| 2018/0221521 A1 | 8/2018 | Shur et al. |
| 2018/0243458 A1 | 8/2018 | Shatalov et al. |
| 2018/0339075 A1 | 11/2018 | Kennedy et al. |
| 2019/0030477 A1 | 1/2019 | Shatalov |
| 2019/0098842 A1 | 4/2019 | Barber, III et al. |
| 2019/0099613 A1 | 4/2019 | Estes et al. |
| 2019/0100445 A1 | 4/2019 | Dobrinsky |
| 2019/0100718 A1 | 4/2019 | Estes et al. |
| 2019/0117811 A1 | 4/2019 | Barber, III |
| 2019/0125907 A1 | 5/2019 | Dobrinsky |
| 2019/0135659 A1 | 5/2019 | Smetona et al. |
| 2019/0201570 A1 | 7/2019 | Dobrisnky et al. |
| 2019/0231912 A1 | 8/2019 | Dobrinsky et al. |

* cited by examiner

ULTRAVIOLET IRRADIATION OF FLUIDS

REFERENCE TO RELATED APPLICATIONS

The present patent application claims the benefit of U.S. Provisional Application No. 62/636,830, which was filed on 28 Feb. 2018, of which is hereby incorporated by reference.

TECHNICAL FIELD

The disclosure relates generally to ultraviolet irradiation, and more specifically, to a solution for using ultraviolet radiation to irradiate liquids and optionally objects in a liquid storage and dispensing device for purposes of sterilization, disinfection, cleaning and other treatment capabilities.

BACKGROUND ART

A water pitcher is one example of a liquid storage and dispensing device that has been implemented with water treatment capabilities that can sterilize, disinfect, and/or clean water while stored in the device. A typical water pitcher with these capabilities utilizes a filter element to remove certain naturally occurring minerals such as chlorine and metals from the water. For example, a water pitcher with an interior gravity filter can filter an incoming flow of water provided to the water pitcher to remove chlorine, metals and other contaminants from the water. The gravity filter, like other filter elements, is good at removing these contaminants from the water, but they are ineffective at treating the water for bacteria and other potential pathogens that can remain in the water.

SUMMARY OF THE INVENTION

This Summary of the Invention introduces a selection of certain concepts in a brief form that are further described below in the Detailed Description of the Invention. It is not intended to exclusively identify key features or essential features of the claimed subject matter set forth in the Claims, nor is it intended as an aid in determining the scope of the claimed subject matter.

Aspects of the present invention are directed to solutions that use ultraviolet radiation to irradiate liquids in a liquid storage and dispensing device for purposes of sterilization, disinfection, cleaning and/or treating. The liquid storage and dispensing device can include any of a number of liquid container devices that can be used to receive a liquid, hold or store the liquid, and serve or dispense the liquid. A pitcher is one example of a liquid container device that can receive, store, and dispense liquids. Other examples of liquid container devices that can be used to receive, store, and dispense liquids and that are suitable for use in any of the various embodiments described herein include, but are not limited to, carafes, decanters, bottles, flasks, jars, vases, growlers, buckets, vessels, cartons, cans, and kettles.

An example of a liquid that is suitable for use with any of these liquid container devices is water. As a result, the liquid container devices can be used to sterilize, disinfect, clean and/or treat water. Although the various embodiments are directed to using a liquid storage and dispensing device to sterilize, disinfect, clean and/or treat water, the embodiments are suitable for use in performing these operations on any of a variety of liquids that may have a need for removal of bacteria, viruses, germs, parasitic agents, micro-organisms, pathogens, and other contaminants that can emerge in drinks or beverages formed from such liquids that can be harmful to those that consume these items. Examples of other liquids that can be sterilized, disinfected, cleaned and/or treated with any of the liquid storage and dispensing devices described herein include, but are not limited to, milk, juices, sodas, wine, fermented drinks (e.g., tea, kombucha, kvass), beer, malt beverages, and distilled liquors.

In the various embodiments, ultraviolet light emitting sources can be deployed with any of the liquid storage and dispensing devices to irradiate the liquid. The ultraviolet light emitting sources can include ultraviolet light emitting devices such as ultraviolet light emitting diodes. Use of ultraviolet light emitting sources with a liquid storage and dispensing device to irradiate a liquid allows the device to be implemented with an ultraviolet illuminator or an ultraviolet illumination system having a straightforward design in comparison to one which utilizes a mercury lamp as an ultraviolet light source. For example, ultraviolet light emitting diodes offer robust technology which does not utilize high voltages which can be the case with mercury lamps. In addition, ultraviolet light emitting diodes can be easily turned on and off. Also, ultraviolet light emitting diodes do not require quartz enclosures which can be the case with other sources such as mercury lamps. Further, ultraviolet light emitting diodes can be implemented in a variety of arrangements about a liquid storage and dispensing device since these ultraviolet light emitting sources can be manufactured as small devices.

The ultraviolet light emitting diodes, like any of the other ultraviolet light emitting sources of the various embodiments, can be configured to operate at peak wavelengths that facilitate sterilization, disinfection, cleaning and treatment of liquids that remove harmful bacteria, viruses, germs, parasitic agents, micro-organisms, pathogens, contaminants and the like. In one embodiment, one or more of the ultraviolet light emitting diodes can be configured to generate ultraviolet C (UV-C) radiation at a set of peak wavelengths that range from 260 nm to 290 nm. In one embodiment, one or more of the ultraviolet light emitting diodes can be configured to generate ultraviolet A (UV-A) and/or visible radiation (also referred to as blue-UV radiation) at a set of peak wavelengths that range from 360 nm to 460 nm. In one embodiment, the ultraviolet light emitting diodes can be configured with some of the ultraviolet light emitting sources generating UV-C radiation and other sources generating blue-UV radiation. In one embodiment, the ultraviolet light emitting diodes can differ by at least one of peak wavelength, polar distribution, angular distribution, size, intensity level, orientation or irradiation pattern.

The ultraviolet light emitting sources can be implemented in one of a number of approaches with a liquid storage and dispensing device to sterilize, disinfect, clean and/or treat a liquid. For example, the ultraviolet light emitting sources can be implemented with a liquid storage and dispensing device such as a liquid container that includes a liquid collection reservoir and a liquid chamber. In one embodiment, the liquid collection reservoir can have an inlet to receive an inflow of a liquid and an outlet to provide an outflow of the liquid to the liquid chamber for storage. A filtering unit can be utilized to filter the inflow of liquid received by the liquid collection reservoir and that is provided to the liquid chamber. In this manner, the filtering unit can remove certain naturally occurring minerals from the liquid such as chlorine and metals from the water. To this extent, the liquid chamber can store the filtered liquid. In one embodiment, the filtering unit can be implemented about the liquid collection reservoir and the liquid chamber in the form of an interior gravity filter. The filtering unit can be located upstream of the liquid collection reservoir, in the reservoir, attached to the reservoir, or in the liquid chamber. The liquid collection reservoir, the filtering unit, and the liquid chamber can take the form of separate components that can be assembled together and disassembled from each other for purposes that can include, but are not limited, to cleaning, repairing, and/or replacing individual components.

In one embodiment, the ultraviolet light emitting sources can be located about the liquid chamber to irradiate the liquid in the liquid chamber with ultraviolet light. For example, the ultraviolet light emitting sources can be placed in a bottom portion of the liquid chamber. In one embodiment, an ultraviolet transparent window can be formed on the inner wall surface at the bottom portion of the liquid chamber over the ultraviolet light emitting sources. The ultraviolet transparent window can include a plurality of distinct ultraviolet transparent windows such that there are distinct ultraviolet transparent windows formed over one of the blue ultraviolet light emitting sources and one of the UV-C light emitting sources. In one embodiment, the ultraviolet transparent windows formed over the blue ultraviolet light emitting sources can include a different material than the ultraviolet transparent windows formed over the UV-C light emitting sources.

In one embodiment, the ultraviolet light emitting sources can have a modular design that is removably attachable with the bottom portion of the liquid chamber. In this scenario, an ultraviolet transparent window, which can also be removably attachable with the bottom portion of the liquid chamber, can separate the bottom portion from the ultraviolet light emitting sources. In one embodiment, the ultraviolet light emitting sources can include a module of sources such that the blue ultraviolet light emitting sources and the UV-C light emitting sources can be removed and replaced from the module and reinstalled with the liquid chamber adjacent to the ultraviolet transparent window. In one embodiment, the ultraviolet light emitting sources (e.g., a set of blue ultraviolet light emitting sources) can be located on an inner wall surface of the liquid chamber.

A control unit can be operatively coupled to the ultraviolet light emitting sources to control the irradiation of the liquid in the liquid chamber with the ultraviolet light emitting sources. In one embodiment, the control unit can control the intensity and the duration of the irradiation as a function of time that the liquid is stored in the liquid chamber and the amount of the liquid that is in the liquid chamber. In addition to controlling the intensity and the duration of the irradiation by the ultraviolet light emitting sources, the control unit can control other irradiation parameters including, but not limited to, the wavelength of the ultraviolet radiation emitted by the sources, the overall dosage of the ultraviolet radiation delivered by the sources, a power setting for operating the sources, and a maximum operating temperature of the sources.

The control unit can include a number of different components that enable it to control the ultraviolet light emitting sources. For example, other components that may be utilized with the control unit can include a timer, an input component and an output component. The timer can be utilized in a number of different manners. For example, the timer can be configured to specify treatment times for operating the ultraviolet light emitting sources in order to ensure that the sources deliver a sufficient dosage to the liquid. The timer can also be used to record the amount of time that a liquid resides in the liquid chamber per data obtained by a liquid sensor and processed by the control unit. In this manner, the control unit can direct the ultraviolet light emitting sources to irradiate the liquid if it has been in the liquid chamber over a predetermined time that can lead to the rise of certain contaminants in the liquid or about the surface of the liquid chamber. For example, the control unit can activate a set of UV-C light emitting sources after the timer measures that the liquid has resided in the liquid chamber for a predetermined time duration in order to begin an irradiation treatment of the liquid.

The input component and the output component, which can take the form of a user input/output component, can facilitate user interaction with the control unit to control the irradiation of the liquid in the liquid chamber with the ultraviolet light emitting sources. For example, the user input/output component can receive user input that adjusts one or more irradiation parameters associated with the ultraviolet light emitting sources. The user input/output component can also be configured to generate information indicative of the irradiation of the liquid in the liquid chamber by the ultraviolet light emitting sources. The information can include at least one of displaying an indication that the ultraviolet light emitting sources are irradiating the liquid in the liquid chamber, displaying an indication of one or more irradiation parameters (e.g., radiative dose delivered to liquid) associated with the sources, or displaying an indication of a date of the most recent irradiation treatment by the ultraviolet light emitting sources. The timer and the user input/output component can be integrated with the control unit and/or the components can be implemented to operate in conjunction with the control unit, the ultraviolet light emitting sources and other components (e.g., sensors, other sources).

The liquid storage and dispensing device of the various embodiments can be configured with one of a number of optical elements that can facilitate the irradiation of the liquid in the liquid chamber for purposes of sterilization, disinfection, cleaning and/or treating of the liquid and/or internal surfaces of the components of the device for eradicating harmful bacteria, viruses, germs, parasitic agents, micro-organisms, pathogens, contaminants, and the like. In one embodiment, at least one optical element can be deployed to distribute the ultraviolet light emitted from the ultraviolet light emitting sources about the liquid in the liquid chamber. For example, the optical element can include at least one of a mirror, a reflector, a lens (e.g., a Fresnel lens and a total internal reflection (TIR) lens), ultraviolet transparent wave guiding material, scattering elements, or a diffusive element.

In one embodiment, a light guiding layer can be optically coupled to the ultraviolet light emitting sources to guide the ultraviolet light in a predetermined pattern that optimizes the type of treatment that is desired. In a scenario in which the ultraviolet light emitting sources are located on the inner wall surface of the liquid chamber, the light guiding layer can be placed about the sources to guide or propagate light through a region of the layer before irradiating the liquid in the chamber. In one embodiment, the light guiding layer can include one or more ultraviolet transparent layers. The ultraviolet transparent layers can have at least one of roughness domains or diffusive domains that allow extraction of the ultraviolet light from the light guiding layer to the liquid in the liquid chamber. In one embodiment, the ultraviolet transparent layers can include glass.

In one embodiment, the light guiding layer can have scattering elements that interact with the ultraviolet light propagating through the layer and redirect it to the liquid in the liquid chamber.

In one embodiment, the liquid storage and dispensing device can utilize a reflective layer to reflect the ultraviolet light generated from the ultraviolet light emitting sources. For example, the inner wall surfaces of the liquid chamber can have at least one reflective layer to reflect the ultraviolet light generated from the ultraviolet light emitting sources specularly or diffusively. The at least one reflective layer can include a fluoropolymer layer or an aluminum layer. In one embodiment, the at least one reflective layer can include UV-A or UV-C reflective material.

The aforementioned optical elements can be arranged about the liquid storage and dispensing device in any of a number of configurations. For example, these optical elements can be disposed about the liquid collection reservoir, the liquid chamber and the ultraviolet light emitting sources in a number of locations that include, but are not limited to, on an internal wall of the liquid chamber, on an external wall of the chamber, or suspended within the chamber.

The liquid storage and dispensing device can be formed of materials that can facilitate the irradiation of the liquid for purposes of sterilization, disinfection, cleaning, and/or treating the liquid and/or surfaces of the device for removing harmful bacteria, viruses, germs, parasitic agents, microorganisms, pathogens, contaminants, and the like. For example, the liquid collection reservoir and the liquid chamber can include inner wall surfaces that have a bio-resistance to bacterial growth and are chemically inert to ultraviolet light. In one embodiment, the inner wall surfaces of the liquid collection reservoir and the liquid chamber can include an ultraviolet absorbing, non ultraviolet degrading material. The liquid collection reservoir and the liquid chamber can also have ultraviolet transparent material that emits ultraviolet light from the ultraviolet light emitting sources while preventing humidity from penetrating the device and damaging the sources.

The various embodiments can include at least one sensor configured to detect operational conditions associated with the irradiation of the liquid in the liquid chamber by the ultraviolet light emitting sources. A number of different sensors can be used singly or in a multiple of combinations to detect operational conditions of the irradiation. The sensors can include, but are not limited to, a liquid sensor to measure a liquid characteristic of the liquid, a liquid transparency sensor to measure the transparency of the liquid in the liquid chamber, a liquid level sensor to measure the level of the liquid in the liquid chamber, a liquid weight sensor to measure the weight of the liquid, a fluorescent sensor to detect the fluorescence emissivity of the liquid after irradiation by one or more of the ultraviolet light emitting sources. Other sensors can include a temperature sensor to detect the temperature about the liquid chamber, a pressure sensor to detect the pressure of the liquid with respect to the liquid chamber, a humidity sensor to detect the humidity about the liquid chamber and/or the liquid collection reservoir, an ultraviolet radiation sensor to detect the ultraviolet intensity of the liquid, and a chemical sensor to detect chemical components in the liquid.

The control unit can obtain data from any of the sensors and use this data to control the irradiation of the liquid. In this manner, the ultraviolet light emitting sources, the control unit and the sensors provide the various embodiments with a feedback mechanism that facilitates monitoring the irradiation of the liquid. For example, this feedback mechanism enables the control unit to determine a presence of harmful contaminants about the liquid based on the conditions detected by the sensor(s). This allows the control unit to direct the ultraviolet light emitting sources to irradiate the liquid at locations where there is a presence of harmful contaminants for removal and suppression thereof.

In one embodiment, the control unit can determine whether the intensity of the fluorescent signal detected by the fluorescent sensor is indicative of a contamination condition present in the liquid in the liquid chamber. In this manner, the control unit can activate the ultraviolet light emitting sources to perform a disinfection operation on the liquid in the liquid chamber in response to determining the contamination condition. In one scenario, the ultraviolet light emitting sources can direct a set of blue ultraviolet light emitting sources and/or UV-C light emitting sources to perform the disinfection operation. For example, the control unit can direct the set of blue ultraviolet light emitting sources to continuously radiate the liquid in the liquid chamber for a predetermined prolonged period of time to inhibit biological growth and the set of UV-C light emitting sources to radiate the liquid in a pulsed regime to reduce biological activity below a target level.

In addition, the control unit can be used to monitor the irradiation of the liquid with feedback from the conditions detected by any of the sensors. To this extent, the control unit can adjust any of the aforementioned irradiation parameters of the ultraviolet light emitting sources as a function of conditions detected by the sensors. For example, a fluorescent sensor can be configured to detect the intensity, the dosage, and the wavelength of the ultraviolet light that irradiates the liquid in the liquid chamber. To this extent, the fluorescent sensor can provide this data to the control unit which can use the data to determine whether the irradiation is sufficient to perform the desired treatment of the liquid. If necessary, the control unit can adjust the irradiation parameters of the ultraviolet light emitting sources accordingly to ensure that the desired treatment is attained.

In one embodiment, the control unit can operate in conjunction with an ultraviolet radiation sensor and a fluorescent sensor. For example, the ultraviolet radiation sensor can be configured to detect the ultraviolet intensity of the liquid in the liquid chamber after being irradiated with ultraviolet radiation from a first ultraviolet light emitting source or set of sources, while the fluorescent sensor can be configured to detect the fluorescent illumination intensity of the liquid after being irradiated by a second ultraviolet light emitting source or set of sources. In this manner, the control unit can receive signals indicative of the conditions detected by the ultraviolet radiation sensor and the fluorescent sensor, and determine a liquid transparency of the liquid and a density level of a particular contaminant. If the control unit determines that the contaminant density level is too high (e.g., the contaminant density level satisfies a predetermined threshold), then it can activate the operation of the ultraviolet light emitting sources to eradicate the particular contaminant.

The liquid storage and dispensing device of the various embodiments can be further configured with other components that complement the irradiation of the liquid in order to further enhance the sterilization, disinfection, cleaning and/or treatment. For example, a liquid mixing element can be deployed to circulate the liquid in the liquid chamber prior to or during irradiation by the ultraviolet light emitting sources. To this extent, the control unit can be configured to activate the liquid mixing element during the irradiation of the liquid in the liquid chamber with the plurality of ultraviolet light emitting sources or prior to the irradiation. In one scenario, the control unit can be configured to periodically activate the liquid mixing element to provide periodic excitation of the liquid in the liquid chamber.

The irradiation of the liquid by the liquid storage and dispensing device can also be enhanced by using other sources in addition to the ultraviolet light emitting sources. For example, at least one visible light emitting source can be used to emit visible light to the liquid in the liquid chamber. In one embodiment, at least one fluorescent radiation source can be used to emit fluorescent radiation to the liquid in the liquid chamber. To this extent, the visible light emitting source and the fluorescent radiation source can aid the ultraviolet light emitting sources in disinfecting any harmful contaminants from the liquid and suppressing further growth.

In one embodiment, a photocatalyst material can be used with any of the various embodiments to facilitate the irradiation of the liquid or surfaces about the liquid collection reservoir and the liquid chamber. For example, the photocatalyst material can include an ultraviolet active photocatalyst located on an inner wall surface of the liquid chamber. The ultraviolet active photocatalyst is configured to undergo a photocatalytic reaction in response to being irradiated by ultraviolet light. The photocatalytic reaction facilitates removal and suppression of any harmful contaminants present in the liquid and/or on the inner wall surface of the liquid chamber.

In addition to having ultraviolet light emitting sources located about the liquid chamber, the various embodiments of the liquid storage and dispensing device can have additional ultraviolet light emitting sources about a section of the device where the liquid is dispensed from the device. For example, a liquid storage and dispensing device in the form of a pitcher can have ultraviolet light emitting sources located about a liquid dispenser component fluidly coupled to the liquid chamber that dispenses treated liquid from the liquid chamber. The liquid dispenser component can have a passage that receives liquid from the liquid chamber, a spout to facilitate pouring of the liquid from the device, and a channel that carries liquid from the passage to the spout. In one embodiment, the liquid dispenser component can have a set of ultraviolet light emitting sources located about the channel to further irradiate the liquid flowing through the passage from the liquid chamber to the spout. For example, the set of ultraviolet light emitting sources located about the channel can include UV-C light emitting sources.

The set of ultraviolet light emitting sources located about the channel can be controlled by the control unit. For example, the control unit can activate the ultraviolet light emitting sources located about the channel in response to data obtained by a sensor used with the liquid dispenser component. In one embodiment, a tilt sensor can be configured to detect an orientation angle of the channel. In this manner, the control unit can activate the set of ultraviolet light emitting sources located about the channel in response to determining that the orientation angle detected by the tilt sensor exceeds a predetermined angle. This allows the set of ultraviolet light emitting sources located about the channel to irradiate the liquid as the liquid flows from the passage through the channel to the spout. In one embodiment, the control unit can periodically direct the set of ultraviolet light emitting sources located about the channel to irradiate the liquid dispenser component in instances where liquid is not flowing therethrough.

The liquid storage and dispensing device of the various embodiments described herein can have a power component that supplies power to the ultraviolet light emitting sources, the sensor(s), the control unit and any other components (e.g., the timer, the user input/output component). In one embodiment, the power component can include a power station that is removably attachable with the liquid chamber. For example, the power station can include an insertable contact that is removably attachable with a bottom portion of the liquid chamber. In one embodiment, the power component can be integrated about the liquid collection reservoir and the liquid chamber.

In addition to irradiating liquids, the liquid storage and dispensing device of the various embodiments can be utilized to irradiate objects that are sized for placement in the device for purposes of sterilization, disinfection, cleaning and/or treatment in instances of which the device is unoccupied with a liquid. In this manner, the ultraviolet light emitting sources can be used to remove harmful bacteria, viruses, germs, parasitic agents, micro-organisms, pathogens, contaminants, and the like. For example, objects like utensils, toothbrushes, razors, etc., that can have a buildup of harmful contaminants can be placed in an empty liquid chamber of the liquid storage and dispensing device and covered up by the liquid collection reservoir, so that the ultraviolet light emitting sources can be deployed to irradiate these items.

A first aspect of the invention provides a liquid storage and dispensing device, comprising: a liquid collection reservoir to receive an inflow of a liquid, the liquid collection reservoir having an inlet to receive the inflow of the liquid and an outlet to provide an outflow of the liquid; a filtering unit to filter the inflow of liquid received by the liquid collection reservoir; a liquid chamber to store liquid filtered by the filtering unit; a plurality of ultraviolet light emitting sources located about the liquid chamber to irradiate the liquid in the liquid chamber with ultraviolet light; and a control unit, operatively coupled to the plurality of ultraviolet light emitting sources to control the irradiation of the liquid in the liquid chamber with the plurality of ultraviolet light emitting sources, wherein the control unit is configured to control an intensity and a duration of the irradiation as a function of time that the liquid is stored in the liquid chamber and an amount of the liquid that is in the liquid chamber.

A second aspect of the invention provides a liquid container, comprising: a liquid collection reservoir to receive an inflow of a liquid, the liquid collection reservoir having an inlet to receive the inflow of the liquid and an outlet to provide an outflow of the liquid; a filtering unit to filter the inflow of liquid received by the liquid collection reservoir; a liquid chamber to store liquid filtered by the filtering unit; a plurality of ultraviolet light emitting sources located about the liquid chamber to irradiate the liquid in the liquid chamber with ultraviolet light, the plurality of ultraviolet light emitting sources including a set of blue ultraviolet light emitting sources configured to operate at a wavelength ranging from 360 nm to 460 nm and a set of ultraviolet-C (UV-C) light emitting sources configured to operate at a wavelength ranging from 260 nm to 290 nm; and a control unit, operatively coupled to the plurality of ultraviolet light emitting sources to control the irradiation of the liquid in the liquid chamber with the plurality of ultraviolet light emitting sources, wherein the control unit directs the set of blue ultraviolet light emitting sources to continuously radiate the liquid in the liquid chamber for a predetermined prolonged period of time to inhibit biological growth and the set of UV-C light emitting sources to radiate the liquid in a pulsed regime to reduce biological activity below a target level.

A third aspect of the invention provides a liquid pitcher, comprising: a liquid collection reservoir to receive an inflow of a liquid, the liquid collection reservoir having an inlet to receive the inflow of the liquid and an outlet to provide an outflow of the liquid; a filtering unit to filter the inflow of liquid received by the liquid collection reservoir; a liquid chamber to store liquid filtered by the filtering unit; a first set of ultraviolet light emitting sources located about the liquid chamber to irradiate the liquid in the liquid chamber with ultraviolet light, the first set of ultraviolet light emitting sources including blue ultraviolet light emitting sources and ultraviolet-C (UV-C) light emitting sources; a liquid dispenser component fluidly coupled to the liquid chamber that dispenses liquid from the liquid chamber, the liquid dispenser component having a passage that receives liquid from the liquid chamber, a pour spout to facilitate pouring of the liquid, a channel that carries liquid from the passage to the pour spout, and a second set of ultraviolet light emitting sources comprising UV-C light emitting sources located about the channel to further irradiate the liquid flowing through the passage from the liquid chamber to the pour spout; a control unit, operatively coupled to the first and second set of ultraviolet light emitting sources to control the irradiation of the liquid; and a user input/output component configured to facilitate user interaction with the control unit to control the irradiation of the liquid with at least one of the first set of ultraviolet light emitting sources or the second set of ultraviolet light emitting sources.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 3A shows a schematic of a liquid storage and dispensing device having ultraviolet light emitting sources for irradiating liquid or objects stored in the device with sensors to detect operational conditions associated with the irradiation, and a liquid mixing element to circulate liquid stored in the device according to an embodiment, while

FIG. 4A shows a schematic of a liquid storage and dispensing device having ultraviolet light emitting sources for irradiating liquid or objects stored in the device with sensors to detect operational conditions and optical elements in a region of a liquid chamber of the device to facilitate the irradiation according to an embodiment, while

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

Figure 1:
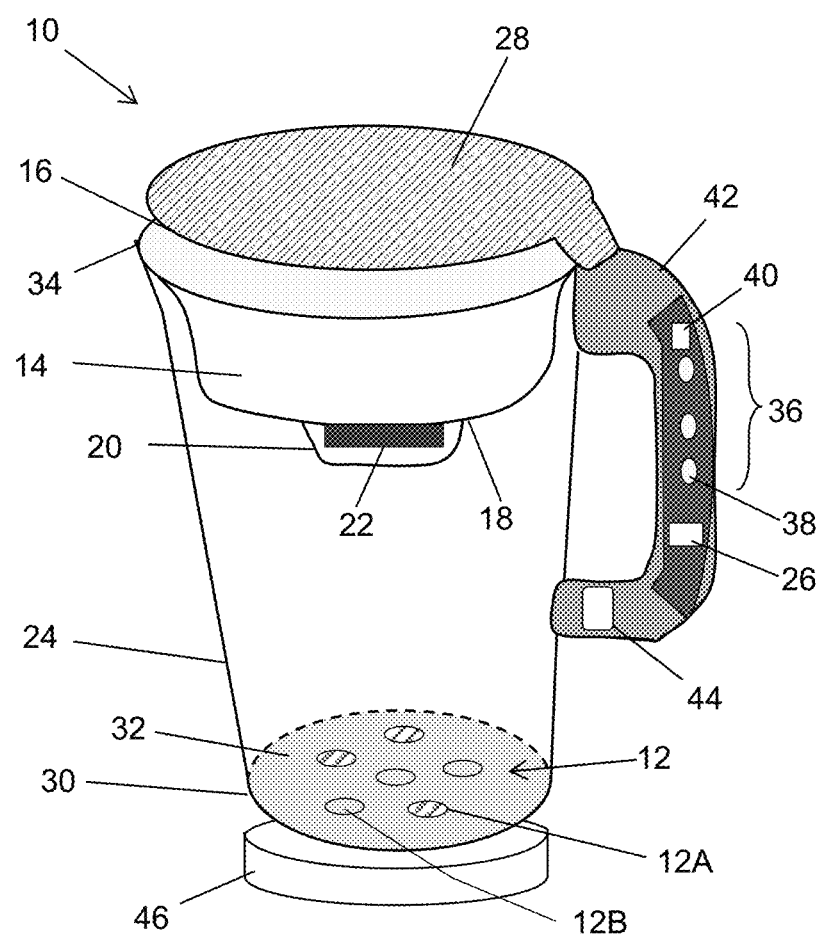
FIG. 1 shows a schematic of a liquid storage and dispensing device having ultraviolet light emitting sources for irradiating liquid or objects stored in the device according to an embodiment.

As indicated above, aspects of the invention are directed to solutions that use ultraviolet radiation to irradiate liquids and optionally objects in a liquid storage and dispensing device for purposes of sterilization, disinfection, cleaning and/or treating of microorganisms, parasitic agents, bacteria, viruses, germs or other harmful contaminants. Ultraviolet irradiation of a body or volume of liquid or a surface of an object can entail sanitizing, disinfecting, and/or sterilizing. Sanitizing generally means reducing the number of bacterial contaminants to a predetermined safe level. Disinfecting generally means destroying pathogenic and other types of microorganisms, while sterilizing can be more extensive in that it kills all microbial forms and/or includes destroying the ability of the microbial forms to reproduce.

Ultraviolet radiation, which can be used interchangeably with ultraviolet light, means electromagnetic radiation generally described as having a wavelength ranging from approximately 10 nm to approximately 400 nm. Within this range, there is ultraviolet-A (UV-A) electromagnetic radiation generally described as having a wavelength ranging from approximately 315 nm to approximately 400 nm, ultraviolet-B (UV-B) electromagnetic radiation generally described as having a wavelength ranging from approximately 280 nm to approximately 315 nm, and ultraviolet-C (UV-C) electromagnetic radiation generally described as having a wavelength ranging from approximately 100 nm to approximately 280 nm. It is understood that a light emitting source configured to operate in a particular range can emit ultraviolet radiation in an adjacent range. For example, as used herein, a UV-C source can also emit UV-B radiation, e.g., 280 nm to 290 nm. As used herein, blue-UV radiation includes at least a portion of the UV-A electromagnetic radiation as well as higher wavelength visible light, e.g., visible light having a wavelength ranging from approximately 400 nm to approximately 460 nm (360 nm to 460 nm in a more particular embodiment).

Generally, ultraviolet radiation, and in particular, UV-B radiation and UV-C radiation is "germicidal," i.e., it deactivates the DNA of bacteria, viruses and other pathogens, and thus, destroys their ability to multiply and cause disease. This effectively results in sterilization of the microorganisms. Specifically, UV-B radiation and UV-C radiation cause damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. Ultraviolet radiation with a wavelength of approximately between about 250 nm to about 290 nm provides the highest germicidal effectiveness, while an ultraviolet radiation between about 260 nm to about 310 nm is sufficient for providing overall germicidal effectiveness, and ultraviolet radiation between 250 nm to 280 nm is a range for facilitating sterilization and disinfection of a vast amount of object and fluid that can develop the presence of contaminants. While susceptibility to ultraviolet radiation varies, exposure to ultraviolet energy in the above range for about 20 to about 34 milliwatt-seconds/cm$^2$ is adequate to deactivate approximately 99 percent of the pathogens.

As used herein, a material/structure/layer is considered to be "reflective" to ultraviolet light of a particular wavelength when the material/structure/layer has an ultraviolet reflection coefficient of at least 30 percent for the ultraviolet light of the particular wavelength. A highly ultraviolet reflective material/structure/layer has an ultraviolet reflection coefficient of at least 80 percent. Furthermore, a material/structure/layer is considered to be "transparent" to ultraviolet radiation of a particular wavelength when the material/structure/layer allows at least ten percent of radiation having a target wavelength, which is radiated at a normal incidence to an interface of the material/structure/layer to pass there through.

The liquid storage and dispensing devices as described in the various embodiments can include a number of components. These components are described below in more detail, some of which may be optional, facilitate the treatment of liquids and optionally objects. The modalities used with the various liquid storage and dispensing devices described herein including its respective components can include any now known or later developed approaches that incorporate the concepts of the embodiments described below in more detail.

The description that follows may use other terminology herein for the purpose of only describing particular embodiments and is not intended to be limiting of the disclosure. For example, unless otherwise noted, the term "set" means one or more (i.e., at least one) and the phrase "any solution" means any now known or later developed solution. The singular forms "a," "an," and "the" include the plural forms as well, unless the context clearly indicates otherwise. It is further understood that the terms "comprises," "comprising," "includes," "including," "has," "have," and "having" when used in this specification, specify the presence of stated features, integers, steps, operations, elements, and/or components, but do not preclude the presence or addition of one or more other features, integers, steps, operations, elements, components, and/or groups thereof. Additionally, spatially relative terms, such as "on," "below," "above," etc., may be used in reference to the orientation shown in the drawings. It is understood that embodiments of the invention are not limited to any particular orientation of a device described herein. Also, the use of a phrase of the form "at least one of A, B, C . . . or n" to delineate a listing of two or more possible parameters, components, characteristics, factors, etc., means any combination of one or more of A, B, C, n. For example, at least one of A or B means only A, only B, or both A and B.

The description may also list values of parameters of elements, components, objects, materials, layers, structures, and the like, for the purpose of describing further details of particular embodiments. It is understood that, unless otherwise specified, each value is approximate and each range of values included herein is inclusive of the end values defining the range. As used herein, unless otherwise noted, the term "approximately" is inclusive of values within +/−ten percent of the stated value, while the term "substantially" is inclusive of values within +/−five percent of the stated value. Unless otherwise stated, two values are "similar" when the smaller value is within +/−twenty-five percent of the larger value. A value, y, is on the order of a stated value, x, when the value y satisfies the formula $0.1x \leq y \leq 10x$. Unless otherwise stated, as used herein, parameters can have comparable values when the values of the corresponding parameters differ by at most ten percent (five percent in a more specific embodiment).

Turning to the drawings, FIG. 1 shows a schematic of a liquid storage and dispensing device 10 having ultraviolet light emitting sources 12 for irradiating liquid and/or surfaces of the components of the device, and optionally objects stored in the device for purposes of sterilization, disinfection, cleaning and/or treating. Irradiation of liquid, surfaces of the components of the device, and/or objects placed in the device is useful for eradicating harmful bacteria, viruses, germs, parasitic agents, micro-organisms, pathogens, contaminants and the like.

The liquid storage and dispensing device 10 depicted in FIG. 1, as well as the other embodiments described herein, is directed to a pitcher such as for example, a water pitcher (e.g., a water purification pitcher, a water treatment pitcher, a water filtration pitcher, etc.). However, it is understood that the liquid storage and dispensing devices of the various embodiments can include any of a number of liquid container devices that can be used to receive a liquid, hold or store the liquid, and serve or dispense the liquid. Other examples of liquid container devices, besides a pitcher, that can be used to receive, store, and dispense liquids, and that are suitable for use in any of the various embodiments described herein, can include, but are not limited to, carafes, decanters, bottles, flasks, jars, vases, growlers, buckets, vessels, cartons, cans, kettles, and the like.

Water is an example of a liquid that is suitable for use with any of the aforementioned liquid container devices. As a result, the liquid container devices that can be used as liquid storage and dispensing devices per any of the various embodiments, have the capability to sterilize, disinfect, clean and/or treat the water prior to consumption. Although the various embodiments are directed to using a liquid storage and dispensing device to sterilize, disinfect, clean and/or treat water, the embodiments are suitable for use in performing these operations on any of a variety of liquids that may have a need for removal of bacteria, viruses, germs, parasitic agents, micro-organisms, pathogens, and other contaminants that can emerge in drinks or beverages formed from such liquids that can be harmful to those that consume these items. Examples of other liquids that can be sterilized, disinfected, cleaned and/or treated with any of the liquid storage and dispensing devices described herein can include, but are not limited to, milk, juices, sodas, wines, fermented drinks (e.g., tea, kombucha, kvass), beer, malt beverages, and distilled liquors.

As shown in FIG. 1, the liquid storage and dispensing device 10 can include a liquid collection reservoir 14 to receive an inflow of a liquid. In one embodiment, the liquid collection reservoir 14 can have an inlet 16 to receive the inflow of the liquid and an outlet 18 to provide an outflow of the liquid. A filtering unit 20 having a filter element 22 can filter the inflow of liquid received by the liquid collection reservoir 14. A liquid chamber 24 receives the liquid filtered by the filter element 22 of the filtering unit 20. The ultraviolet light emitting sources 12, which are located about the liquid chamber 24 can irradiate the liquid in the liquid chamber with ultraviolet light. A control unit 26 is operatively coupled to the ultraviolet light emitting sources 12 to control the irradiation of the liquid in the liquid chamber 24 by the ultraviolet light emitting sources. In one embodiment, the control unit 26 is configured to control an intensity and a duration of the irradiation as a function of time that the liquid is stored in the liquid chamber 24 and the amount of the liquid that is in the liquid chamber.

Removal of a cover 28 that is sized to correspondingly mate with a top portion of the liquid collection reservoir 14 allows an inflow of liquid to enter the inlet 16. After a desired amount of liquid has been provided to the liquid collection reservoir 14, the cover can be placed back over the top portion of the reservoir to prevent unintended spillage. In addition to allowing an inflow of liquid to enter the liquid collection reservoir 14 through the inlet 16, removal of the cover 28 permits access to the liquid collection reservoir 14, filtering unit 20 including the filter element 22, the liquid chamber 24 and the ultraviolet light emitting sources 12, for purposes that can include, but are not limited to, cleaning, replacing, removing and repairing any of these components. To this extent, removal of the cover 28 to provide access to these other components for purposes of cleaning, replacing, removing and repairing these items separately affords the liquid storage and dispensing device 10 with the benefit of having an assembly/disassembly arrangement of components. As used herein, an assembly/disassembly arrangement of components means a number of parts or subassemblies that can be put together to form a device and perform a specific function within the operation of the device, and have the capability of being disassembled from the device without destruction.

It is understood that the cover 28 depicted in FIG. 1 represents only one possible configuration that may be used with the liquid storage and dispensing device 10. For instance, the cover 28 can have an openable member such as a door or hatch, located at a top surface of the cover that opens relative to the cover by for example, pivoting or sliding relative to the cover. In one embodiment, the openable member can be movably connected to the cover by, for example, a hinge and/or any other suitable connection such as a sliding connection that allows the openable member to pivot or slide between open and closed positions. In one embodiment, the openable member can be completely removable from the cover 28. For example, the openable member and/or cover 28 may include interlocking structures (e.g., latches, catches, etc.) so that the openable member may releasably interlock with the cover with the openable member in the closed position, which can inhibit unintended opening of the openable member. In one embodiment, the openable member may include a grasping structure that allows a user to manually grasp the openable member and move the openable member relative to the cover 28. The openable member in all of these embodiments would be coupled to the inlet 16 so that the liquid collection reservoir 14 can receive an inflow of liquid.

Although not shown in FIG. 1, the liquid collection reservoir 14 can have a collection chamber that is in fluid communication with the inlet 16 and the outlet 18. In the embodiment depicted in FIG. 1, the collection chamber can accumulate a volume of liquid that is substantially larger than the amount of the liquid that flows out of the liquid collection reservoir through the outlet 18 to the filtering unit 20 and the filter element 22. It is understood that in other embodiments in which liquid is provided to the liquid collection reservoir 14 in other approaches that do not involve removing the cover 28 (e.g., the use of an openable member in the cover), the inlet 16 in these embodiments would receive an inflow of liquid that is substantially smaller in volume in comparison to the amount that the collection chamber could hold prior to the liquid flowing out of the reservoir through the outlet 18 into the filtering unit 20.

In one embodiment, the filtering unit 20 including the filter element 22 can be implemented about the liquid collection reservoir 14 and the liquid chamber 24 in the form of a gravity filtering unit. To this extent, the liquid that accumulates in the collection chamber of the liquid collection reservoir 14 through the inlet 16 will gravity feed through the outlet 18 into the filtering unit 20 where it is filtered by the filter element 22 to remove impurities and other undesirable particles. The filtered liquid is then gravity fed from the filtering unit 20 into the liquid chamber 24. In a scenario in which the liquid used with the liquid storage and dispensing device 10 is water, an inflow of water from sources that include, but are not limited to, tap water, streams, rivers, and the like, is supplied to the liquid collection reservoir 14 via the inlet 16 where it accumulates in the collection chamber and is gravity fed through the outlet 18 into the filtering unit 20 where the water is filtered and subsequently gravity fed to the liquid chamber 24.

The filter element 22 can remove certain naturally occurring minerals from the water such as chlorine and metals as well as a host of particles that have sizes that are typically greater than the pore sizes of the filter element. For example, a filter element with pores sizes that are 1 micron or less can remove undesirable parasitic agents such as *Cryptosporidium* and *Giardia*. The filter element 22 that can be used with the filtering unit 20 can include any of a number of well-known filter elements used to filter or purify water. For example, the filter element 22 can include a carbon filter, a ceramic filter, a sediment filter, a reverse osmosis filter, etc.

It is understood that the configuration of the liquid collection reservoir 14, the filtering unit 20 and the liquid chamber 24 as depicted in FIG. 1 represents only one arrangement and is not meant to limit this embodiment as well as others described herein. For example, in one embodiment, instead of having the filtering unit 20 and filter element 22 attached to the liquid collection reservoir 14 as depicted in FIG. 1, it can be integrated within the collection reservoir or in the liquid chamber 24. In one embodiment, the filtering unit 20 and the filter element 22 can be placed upstream of the inlet 16 of the liquid collection reservoir 14 to prefilter the liquid before it accumulates in the collection reservoir.

The filtered liquid that is stored in the liquid chamber 24 can be irradiated by the ultraviolet light emitting sources 12. The ultraviolet light emitting sources 12 can comprise any combination of one or more ultraviolet radiation emitter. For example, the set of ultraviolet light emitting sources 12 can include a high intensity ultraviolet lamp (e.g., a high intensity mercury lamp), a discharge lamp, ultraviolet light emitting diodes (LEDs), deep ultraviolet LEDS, super luminescent LEDs, laser diodes, and/or the like. In an embodiment, the ultraviolet light emitting sources can include a set of light emitting diodes manufactured with one or more layers of materials selected from the group-III nitride material system (e.g., $Al_xIn_yGa_{1-x-y}N$, where $0 \leq x$, $y \leq 1$, and $x+y \leq 1$ and/or alloys thereof). Additionally, the set of ultraviolet light emitting sources 12 can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures include, but are not limited to, a wave guide, a plurality of ultraviolet fibers, each of which terminates at an opening, a diffuser, and/or the like. In addition, optical elements including but not limited to, lenses, prismatic ultraviolet transparent elements, mirror elements (e.g., a parabolic mirror element, an omnidirectional mirror, a planar mirror and/or the like) can be deployed as a primary and/or secondary of optical elements for focusing the radiation in a particular pattern and/or direction from the sources.

The ultraviolet light emitting sources 12 can be configured to operate at peak wavelengths that facilitate sterilization, disinfection, cleaning and treatment of the liquid in the liquid chamber 24 that remove harmful bacteria, viruses, germs, parasitic agents, micro-organisms, pathogens, contaminants and the like. In one embodiment, the ultraviolet light emitting sources 12 can differ by at least one of peak wavelength, polar distribution, angular distribution, size, intensity level, orientation or irradiation pattern in order to facilitate efficient irradiation and/or higher disinfection rates of the liquid in the liquid chamber 24. In embodiments in which the liquid used with the liquid storage and dispensing device 10 is water, the use of the ultraviolet light emitting sources 12 can have significant effects on the sterilization, disinfection, cleaning and/or treatment of the water. For example, the use of the ultraviolet light emitting sources 12 to irradiate the water can provide a reduction of microorganism (e.g., bacterial and/or viral) contamination in the water by at least a factor of two. In one embodiment, the liquid storage and dispensing devices of the various embodiments through the use of the ultraviolet light emitting sources 12 and control unit 26 can provide approximately 99.9% decontamination of the water in the liquid chamber 24.

In one embodiment, as depicted in FIG. 1, the ultraviolet light emitting sources 12 can include a first set of ultraviolet light emitting sources 12A configured to operate at a blue ultraviolet wavelength ranging from 360 nm to 460 nm, and a second set of ultraviolet light emitting sources 12B configured to operate at an ultraviolet-C (UV-C) wavelength ranging from 260 nm to 290 nm. In another embodiment that provides efficient inactivation of bacterial contaminations, the first set of ultraviolet light emitting sources 12A can operate at a blue ultraviolet wavelength ranging from 360 nm to 430 nm, while the second set of ultraviolet light emitting sources 12B can operate at a UV-C wavelength ranging from 260 nm to 290 nm.

In general, the blue-UV light emitting sources 12A comprise high intensity wide coverage sources that are capable of continuous operation in an efficient matter over a large stretch of time (e.g., several days), while the UV-C light emitting sources 12B can operate at specific wavelengths optimized to treat certain micro-organisms, pathogens, viruses, parasitic agents, and the like. Irradiating the liquid with multiple wavelengths of radiation that is afforded with the use of the blue ultraviolet light emitting sources 12A and the UV-C light emitting sources 12B enables the ultraviolet light emitting sources 12 to deliver a variety of irradiation treatments. For example, the blue ultraviolet light emitting sources 12A can deliver blue-UV radiation to the liquid over a prolonged period of time that can range from tens of minutes to tens of hours, while the UV-C light emitting sources 12B can emit UV-C radiation to perform a more intense ultraviolet irradiation treatment at a short burst of intensity that lasts at most a few minutes. In this manner, the UV-C radiation can rapidly bring any microbial activity in the liquid to within appropriate limits, while the blue-UV radiation can maintain microbial activity within limits over an extended period of time.

It is understood that both UV-C and blue-UV light emitting sources are capable of producing a distributed intensity over an area of the liquid chamber 14 or a volume of liquid in the chamber at a certain distance from the sources, where distances can range from a few centimeters to several meters. As used herein, irradiation of a volume or a location defines a region that is impinged by radiation, wherein the intensity of radiation deposited at the boundary of the region is at most 10% of the intensity of light deposited at the center of the region. It is understood that the position of irradiated volumes or locations can be adjusted to result in separate volumes or locations, wherein "separate" means that the intensity of radiation between the volumes or locations is no larger than 10% of the intensity in the center of the volumes or locations. In addition, these volumes or locations of irradiation can be designed to have relatively uniform radiation, with radiation intensity varying through the volume or location of no more than several times between any two points within the volume or location.

The ultraviolet light emitting sources 12 can be located about the liquid chamber 24 to irradiate the liquid in the liquid chamber. As used herein, "located about the liquid chamber" means locations that can include on an interior or exterior wall surface of one of the components that form the liquid storage and dispensing device (e.g., the liquid collection reservoir, the filtering unit, the liquid chamber, the handle, the pour spout) or within a predetermined distance away from the device that is capable of delivering radiation to the liquid within the device that is effective at treating the liquid for purposes that include sterilization, disinfection, cleaning and/or treatment. In one embodiment, as shown in FIG. 1, the ultraviolet light emitting sources 12 can be placed in a bottom portion 30 of the liquid chamber 24.

In one embodiment, an ultraviolet transparent window 32 can be formed on the inner wall surface at the bottom portion 30 of the liquid chamber 24 over the ultraviolet light emitting sources 12 to facilitate transmissivity of the light generated from the sources. The ultraviolet transparent window 32 can be formed from one of a variety of materials. For example, the ultraviolet transparent windows 32 can comprise an ultraviolet transparent fluoropolymer that can transmit ultraviolet light. In one embodiment, ultraviolet transparent fluoropolymers that can be used for the ultraviolet transparent window 32 can include EFEP, Cytop®, Teflon®, $SiO_2$, $SiO_2$ derivatives such as moldable silicone, $Al_2O_3$, $CaF_2$, and $MgF_2$. It is understood that other ultraviolet transparent fluoropolymers can be used to form the ultraviolet transparent window 32.

In one embodiment, the ultraviolet transparent window 32 can include a plurality of distinct ultraviolet transparent windows each formed over one of the ultraviolet light emitting sources 12. For instance, in the example depicted in FIG. 1, distinct ultraviolet transparent windows can be formed over each blue ultraviolet light emitting source 12A and each UV-C light emitting source 12B. In one embodiment, the ultraviolet transparent windows formed over the blue ultraviolet light emitting sources 12A can include a different material than the ultraviolet transparent windows formed over the UV-C light emitting sources 12B.

Although the embodiment depicted in FIG. 1 shows the ultraviolet light emitting sources 12 on the inner wall surface at the bottom portion 30 of the liquid chamber 24, it is understood that the sources can be positioned in other locations about the liquid chamber. For example, the ultraviolet light emitting sources 12 can be placed in other portions of the liquid chamber 24 above the bottom portion 30, on an underlying surface of the filtering unit 20, on the exterior walls of the liquid chamber, or near a pour spout 34 used to dispense liquid from the liquid storage and dispensing device 10. Ultraviolet light emitting sources 12 at any of these locations can be used along with those at the bottom portion 30 of the liquid chamber 24 or in place thereof. Further, it is understood that the arrangement possibilities of the ultraviolet light emitting sources 12 is extensive and thus, the embodiment depicted in FIG. 1 as well as other embodiments described herein are not meant to be limited to any one specific configuration. Similarly, the number of ultraviolet light emitting sources 12 at one location can vary, and any number of sources or other components that are depicted in the figures are not meant to be limiting to any of the embodiments described herein.

In addition to being located at multiple locations about the various components of the liquid storage and dispensing device 10, the ultraviolet light emitting sources 12 can be movable, such that the sources can be moved and oriented to direct ultraviolet radiation in a desired manner to effectuate a particular ultraviolet treatment of the liquid in the liquid chamber 24, the interior wall surfaces of any of the components of the device, or an object placed inside for a treatment. For example, the ultraviolet light emitting sources 12 can be configured to be moveable over a predetermined number of degrees of freedom to facilitate irradiation of desired locations about a body of liquid or an object placed inside the liquid storage and dispensing device 10. In one embodiment, the ultraviolet light emitting sources 12 can be placed in the bottom of the device 10 in an orientation that is pointing directly upwards, or slightly tilted to irradiate the sides or inner wall surfaces of the liquid chamber 24.

The liquid storage and dispensing device 10 can be formed of materials that can facilitate the irradiation of the liquid for purposes of sterilization, disinfection, cleaning, and/or treating the liquid and/or surfaces of the device for removing harmful bacteria, viruses, germs, parasitic agents, micro-organisms, pathogens, contaminants, and the like. For example, the liquid collection reservoir and the liquid chamber can include inner wall surfaces that have a bio-resistance to bacterial growth and are chemically inert to ultraviolet light.

In one embodiment, the exterior wall surfaces of the liquid collection reservoir and the liquid chamber can include an ultraviolet absorbing, non ultraviolet degrading material that prevents radiation from escaping outside the liquid storage and dispensing device 10.

In embodiments in which the ultraviolet light emitting sources 12 are located on the interior wall surfaces of components such as the liquid chamber 24, the liquid collection reservoir 14, the filtering unit 20, the sources can be encapsulated to protect these components from environmental factors such as humidity. For example, an ultraviolet transparent material can be used to encapsulate the sources while preventing humidity from penetrating and damaging the sources. In one embodiment, the ultraviolet transparent material can include an ultraviolet transparent fluoropolymer that encapsulates the ultraviolet light emitting sources 12. Ultraviolet transparent fluoropolymers that include, but are not limited to, fluorinated ethylene propylene (FEP), tetrafluoroethylene hexafluoropropylene vinylidene fluoride (THV), polytetrafluoroethylene (PTFE), Cytop®, and/or the like, are examples of ultraviolet transparent material that are suitable for encapsulating and protecting the ultraviolet light emitting sources 12 while allowing the transmission of the light for irradiation purposes.

In one embodiment, the ultraviolet transparent material can comprise an ultraviolet transparent film. For example, the ultraviolet transparent film can cover at least one light emitting side of the ultraviolet light emitting sources 12. However, it is understood that the ultraviolet transparent film can be formed at other locations about the ultraviolet light emitting sources. For example, the ultraviolet transparent film can be adjacent ultraviolet light emitting sources that are configured to emit radiation through a corresponding ultraviolet transparent window to facilitate transmissivity of any light that does not pass through the windows. In one scenario in which the ultraviolet light emitting sources 12 include an ultraviolet light emitting diode die, the ultraviolet transparent film can be placed adjacent to the surface of the die. The ultraviolet transparent film can comprise a thin fluoropolymer film including, but not limited to, EFEP, Cytop®, Teflon®, and/or the like. In an alternative embodiment such elements can comprise $SiO_2$, $Al_2O_3$, $CaF_2$, $MgF_2$, and/or the like.

As noted above, the control unit 26 is configured to control the irradiation of the liquid by the ultraviolet light emitting sources 12. In one embodiment, the control unit 26 can control the intensity and the duration of the irradiation as a function of time that the liquid is stored in the liquid chamber 24 and the amount of the liquid that is in the liquid chamber. In addition to controlling the intensity and the duration of the irradiation by the ultraviolet light emitting sources 12, the control unit 26 can control other irradiation parameters including, but not limited to, the wavelength of the ultraviolet radiation emitted by the sources, the overall dosage of the ultraviolet radiation delivered to a volume of the liquid in the liquid chamber by the sources, a power setting for operating the sources, and a maximum operating temperature of the sources. As explained below in more detail with respect to other embodiments, the control unit 26 can specify and change the irradiation parameters based on operational data obtained from one or more sensors located about the components of the liquid storage and dispensing device 10.

It is understood that the control unit 26 can control the operation of the ultraviolet light emitting sources 12 without the use of any sensors like the embodiment depicted in FIG. 1. For example, the control unit 26 can activate the operation of the ultraviolet light emitting sources 12 in response to a user request received via a user input/output component 36. For example, the user input/output component 36 can be configured to have a variety of different treatment modes that a user can choose from. Each of these treatment modes can be configured to cause the ultraviolet light emitting sources 12 to irradiate the liquid in the liquid chamber 24 or optionally any objects placed in the chamber with radiation of certain wavelengths, intensities, dosage, pattern, distribution and the like that are designed to attain a predetermined type of treatment (e.g., a disinfection, sterilization, eradication of certain bacteria, viruses, parasitic agents, etc.).

The control unit 26 can direct the ultraviolet light emitting sources 12 to perform each of these treatments for a predetermined duration facilitated by the use of a timer that is part of the control unit or a separate component. In one embodiment, the control unit 26 operating in conjunction with the timer can manage the amount of time that the ultraviolet light emitting sources 12 radiate in the UV-C range versus the UV-B range and/or the blue ultraviolet range. For example, in FIG. 1, the control unit 26 operating in conjunction with the timer can manage the amount of time that the blue ultraviolet light emitting sources 12A irradiate the liquid with blue ultraviolet radiation, while the UV-C sources 12B irradiate the liquid with UV-C radiation. The duration and frequency that the ultraviolet light emitting sources 12A and 12B are utilized can be predetermined or can depend on detected condition signals provided to the control unit 26 by any of the sensors utilized to detect operational conditions. To this extent, the control unit 26 and the timer ensure that the ultraviolet light emitting sources 12 irradiate the liquid or objects for the predetermined duration so that a sufficient dosage is delivered.

After irradiation is complete, a notification can be provided to the user via a display, indicator, or the like that can operate in conjunction with the user input/output component 36. In this manner, the user, upon viewing such a display, can then dispense the treated liquid out from the liquid storage and dispensing device 10 via the pour spout 34 for consumption.

In general, the user input/output component 36 facilitates user interaction with the control unit 26 via a set of input buttons, touch screens, and/or the like 38, and at least one output button, screen, display, and/or the like 40, prior to initiating a treatment and/or during an ultraviolet irradiation treatment. In this manner, the user can use any of the inputs 38 to specify various input selections regarding the irradiation parameters (e.g., intensity level, dosage, wavelength, irradiation pattern and duration) for controlling the irradiation of the liquid in the liquid chamber 24 with the ultraviolet light emitting sources 12. For example, after using one of the inputs 38 to activate an irradiation operation, the user can use the inputs to adjust one or more irradiation parameters associated with the ultraviolet light emitting sources 12.

The output 40 part of the input/output component 36 can be configured to generate information to the user that is indicative of the irradiation of the liquid or object in the liquid chamber 24 by the ultraviolet light emitting sources 12. The output can provide the information through one of a number of different modalities that include, but are not limited to, visual textual displays, visible indicator light displays (e.g., flashing lights), and auditory outputs generated by a speaker, and/or the like. For example, the output 40 can include a visual textual display that provides status information on the ultraviolet irradiation of the fluid or an object (e.g., time remaining, the presence of bacteria, viruses, germs, or the like) and the conditions of the object or fluid (e.g., surface changes, fluid appearance changes, presence of contaminants). Other visual textual displays can include, but are not limited to, displaying information on one or more irradiation parameters that are associated with a current irradiation operation (e.g., radiative dose delivered to the liquid), and displaying an indication of a date of the most recent irradiation treatment by the ultraviolet light emitting sources 12. Visible indicator light displays can be utilized to indicate a variety of conditions that include, but are not limited to, whether an ultraviolet irradiation treatment is recommended, whether the object or fluid has been sterilized, disinfected, sanitized, whether an ultraviolet treatment is underway (e.g., an illuminated light), or whether the treatment is over (e.g., absence of an illuminated light).

The control unit 26 and the input/output component 36 can be placed about a liquid storage and dispensing device in one of a variety of locations. For example, as shown in FIG. 1 as well other embodiments depicted in the figures, the control unit 26 and the input/output component 36 can be arranged about the handle 42 of the device. Nevertheless, it is understood that the control unit 26 and the input/output component 36 can be arranged about the liquid storage and dispensing device in other locations instead of the handle 42. For example, in one embodiment, the control unit 26 and the input/output component 36 can be located on the exterior of the liquid storage and dispensing device such as the liquid chamber 24. In one embodiment, the control unit 26 and the input/output component 36 can be located in different locations about the liquid storage and dispensing device. For example, in one embodiment, the control unit 26 can be positioned on exterior wall surface of the liquid chamber 24, while the input/output component 36 can be located on the handle 42.

The liquid storage and dispensing device 10 of FIG. 1 as well as the devices of the other embodiments described herein can have a power component 44 that supplies power to the ultraviolet light emitting sources 12, the control unit 26, the input/output component 36 and any other components (e.g., the timer, sensors) that rely on a power source to operate. The power component 44 can take the form of one or more of a variety of power sources. Examples of power sources that are suitable for use as the power component 44 can include, but are not limited to, one or more batteries (e.g., rechargeable batteries), a vibration power generator that can generate power based on magnetic inducted oscillations or stresses developed on a piezoelectric crystal, a rechargeable device such as a super capacitor.

These examples of power sources can be deployed in a number of locations about the liquid collection reservoir 14 and the liquid chamber 24 of the liquid storage and dispensing device 10. For example, these examples of power sources can be integrated in the handle 42 of the liquid storage and dispensing device as shown in FIG. 1 and other embodiments disclosed herein. The use of the handle 42 to deploy the power sources is only one example, and thus, it is understood that these sources can be positioned in other locations about the liquid storage and dispensing device 10. For example, as shown in FIG. 1 as well as the other embodiments, a power source to the liquid storage and dispensing devices of the various embodiments can include a power station 46 that is removably attachable with the liquid chamber. For example, the power station 46 can include a stand with an insertable electrical contact that is removably attachable with the bottom portion 30 of the liquid chamber 24.

The liquid storage and dispensing devices of the various embodiments can further include a heat dissipating component. To this extent, a heat dissipating component enables the electronic componentry associated with the ultraviolet light emitting sources 12, the control unit 26, the input/output component 36, and other electrical components (e.g., the timer, the power sources, the sensors) to operate efficiently without overheating. Examples of a heat dissipating component can include, but are not limited to, a heat sink, an air fan, and/or other heat dissipating mechanisms, such as liquid heating.

Figure 2:
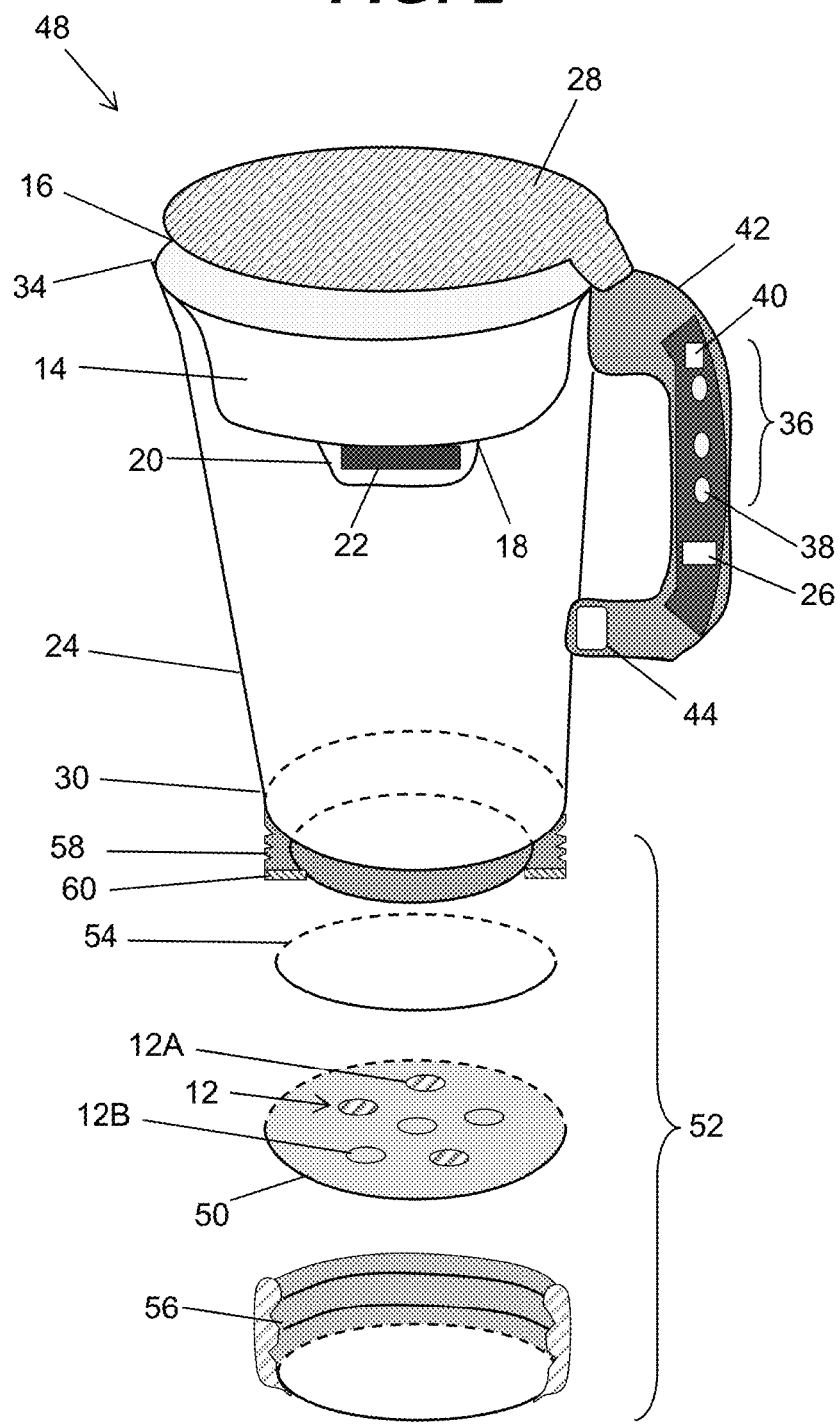
FIG. 2 shows a schematic of a liquid storage and dispensing device having a module of ultraviolet light emitting sources that is removably attachable with a bottom portion of the device according to an embodiment.

FIG. 2 shows a schematic of a liquid storage and dispensing device 48 that is similar to the device 10 depicted in FIG. 1, except that the device 48 utilizes a module 50 of ultraviolet light emitting sources 12 that is removably attachable with the bottom portion 30 of the liquid chamber 24. The module 50 of ultraviolet light emitting sources 12 along with other components can form a bottom base 52 of the liquid storage and dispensing device 48. As shown in FIG. 2, these other components can include an ultraviolet transparent window module 54 that is configured for placement between the bottom region 30 of the liquid chamber 24 and the module 50 of ultraviolet light emitting sources 12. Both of the ultraviolet transparent window module 54 and the module 50 of ultraviolet light emitting sources 12 can be configured for secure placement within a threaded cap 56 that is complementary to mate with a threaded protrusion region 58 extending from the bottom region 30 of the liquid chamber 24. A rubber insert 60 on the threaded protrusion region 58, which is received by the threaded cap can be utilized to prevent leakage of liquid from the liquid chamber 24.

With this configuration, both the module 50 of ultraviolet light emitting sources 12 and the ultraviolet transparent window module 54 can easily be disassembled from the liquid storage and dispensing device 48 by removing the threaded cap 56 from the threaded protrusion region 58 and removing the modules from the cap. In this manner, cleaning, repairing or replacing the module ultraviolet light emitting sources 12 and the ultraviolet transparent window module 54 and reassembling these items back in the liquid storage and dispensing device 48 can be performed quickly and easily.

The ultraviolet transparent window module 54 can be configured to have different positional arrangements with respect to the module 50 of ultraviolet light emitting sources 12 and the bottom region 30 of the liquid chamber. For instance, the ultraviolet transparent window module 54 can be placed over an opening at the bottom region 30 of the liquid chamber 24 by the outward extending rubber insert 60. To this extent, the ultraviolet transparent window module 54 can be placed partly or entirely over the rubber insert 60 to separate the module 50 of ultraviolet light emitting sources 12 from interaction with the liquid (e.g., water) within the liquid chamber 24.

The ultraviolet transparent window module 54 can be formed from a variety of materials that facilitate transmissivity of the light generated from the sources 12. For example, the ultraviolet transparent window module 54 can comprise an ultraviolet transparent fluoropolymer that can transmit ultraviolet light. In one embodiment, ultraviolet transparent fluoropolymer that can be used for the ultraviolet transparent window module 54 can include EFEP, Cytop®, Teflon®, $SiO_2$, $SiO_2$ derivatives such as moldable silicone, $Al_2O_3$, $CaF_2$, and $MgF_2$. It is understood that other ultraviolet transparent fluoropolymers can be used to form the ultraviolet transparent window module 54.

Figure 3A:
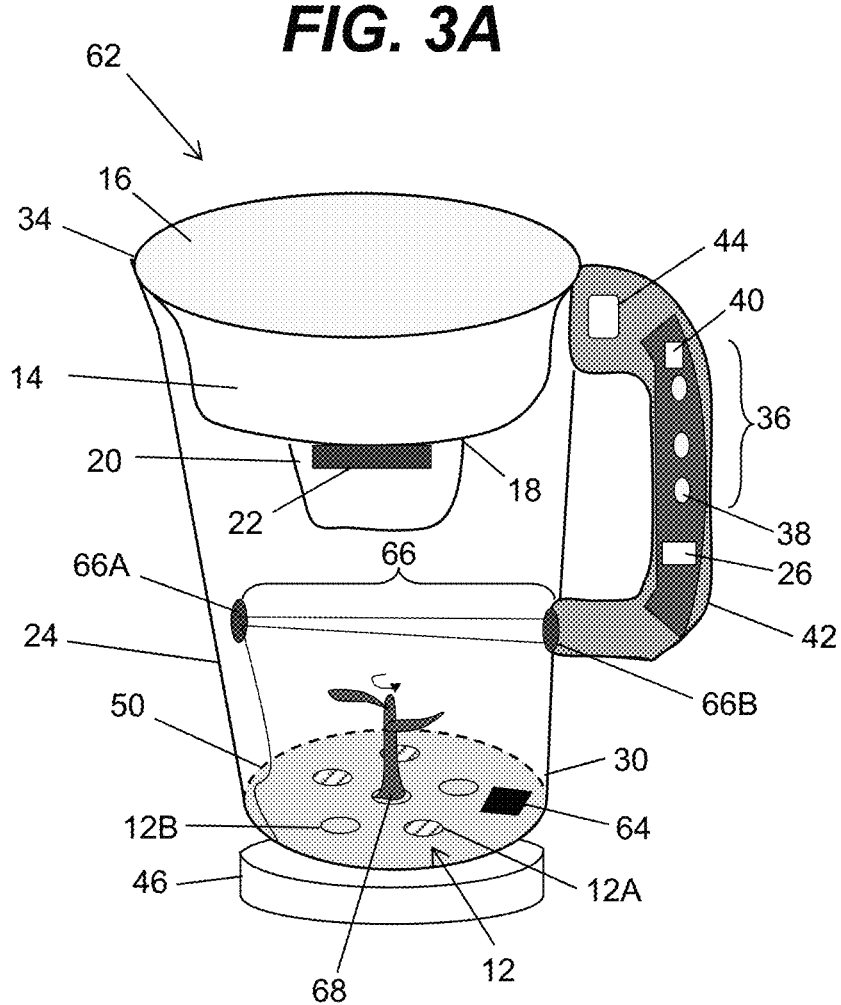

As noted above, the liquid storage and dispensing devices of the various embodiments described herein can utilize one or more sensors to detect operational conditions associated with the liquid and any objects inserted in the liquid chamber, as well as the operational conditions associated with the irradiation of these items by the ultraviolet light emitting sources. FIG. 3A shows an embodiment of a liquid storage and dispensing device 62 in which one or more sensors are utilized. In one embodiment, one or more liquid sensors can be configured about the liquid chamber 24 to measure liquid characteristics of the liquid in the chamber.

For example, in FIG. 3A, one type of liquid sensor that can be deployed with the liquid storage and dispensing device 62 is a liquid weight sensor 64 that is configured to measure the weight of the liquid in the liquid chamber 24. In one embodiment, the liquid weight sensor 64 can be located in the bottom region 30 of the liquid chamber 24 to measure the weight of the liquid. As an example, the liquid weight sensor 64 can be embedded with the module 50 of ultraviolet light emitting sources 12. In one embodiment, the liquid weight sensor 64 can include a pressure sensor.

Although only one liquid weight sensor 64 is depicted in FIG. 3A, it is understood that more than one liquid weight sensor can be utilized. For example, a first liquid weight sensor such as a pressure sensor can be positioned at the base of the liquid, while a second liquid weight sensor which can be another pressure sensor can be positioned external to the liquid to measure the ambient pressure. To this extent, the control unit 26 can use the information from both pressure sensors to determine the weight of the liquid. For example, by subtracting ambient pressure from the total pressure indicated at the base of the liquid, the control unit 26 can determine the actual pressure exerted by the liquid on the first pressure sensor positioned at the base of the liquid. The control unit 26 can then use the actual pressure to calculate of liquid weight.

Another type of liquid sensor that can be used with the liquid storage and dispensing device 62 is a liquid level sensor 66 that is configured to measure the level of the liquid in the liquid chamber 24. As shown in FIG. 3A, the liquid level sensor 66 can comprise two liquid level sensors 66A and 66B positioned at a position above the bottom region 30 of the liquid chamber 24. It is understood that the position of the liquid level sensors 66A and 66B within the liquid chamber 24 can vary, however, it is preferable to have the sensors at least at a level that corresponds to a chamber that is a quarter filled. It is understood that other configurations and arrangements of the liquid level sensors are possible. In one embodiment, instead of using separate liquid weight sensors and liquid level sensors, it is possible to utilize a sensor configuration that can facilitate attaining both measurements. For example, use of the two aforementioned pressure sensors can be used to obtain the liquid level from liquid weight assuming that the density of the liquid is known. If not, then a third pressure sensor can be located in the liquid chamber 24 above the first pressure sensor to measure density of the liquid. In either case, the control unit 26 can use these measurements to obtain the liquid level.

In one embodiment, the control unit 26 can use the measurements obtained from the various liquid sensors to activate the ultraviolet light emitting sources 12 to irradiate the liquid in the liquid chamber 24 if conditions warrant a treatment. For example, the control unit 26 in conjunction with the timer, can determine the amount of time that the liquid has resided in the liquid chamber 24 as a function of at least one of the liquid weight or liquid level measurements. In one scenario, the control unit 26 can activate the set of UV-C light emitting sources 12B after the timer measures that the liquid has resided in the liquid chamber 24 for a predetermined time duration (e.g., multiple hours). In an embodiment, a user can instruct the control unit 26 to activate the set of UV-C light emitting sources 12B, e.g., when the liquid is suspected of and/or known to include contaminants.

Although FIG. 3A shows the liquid storage and dispensing device 62 utilizing the liquid weight sensor 64 and the liquid level sensor 66, it is understood that other liquid sensors can be used in place of these sensors or used in combination to obtain a multiple of liquid characteristic measurements. For example, a liquid transparency sensor (e.g., a water transparency meter) is another type of liquid sensor that can be used to measure the transparency of the liquid in the liquid chamber 24. For example, a liquid transparency sensor can emit light through a portion of the liquid in the liquid chamber 24 toward a light sensor. Based on variations in the quantity of light sensed by the sensor, the control unit 26 can determine the transparency of the liquid. If the control unit 26 determines that the liquid has an insufficient transparency for the particular liquid, then the control unit 26 can activate one or both of the blue ultraviolet light emitting sources 12A or the UV-C light emitting sources 12B to irradiate the liquid. It is understood that the selection of the sources and the irradiation parameters will depend on the liquid conditions measured by the liquid level sensor and any other sensors used to obtain conditions of the liquid.

The liquid storage and dispensing device 62 of FIG. 3A as well as the devices of the other embodiments can utilize other types of sensor besides, or in addition to the aforementioned liquid sensors to detect operational conditions. The sensors can be positioned in a variety of locations about the liquid chamber 24, the liquid collection reservoir 14, and the filtering unit 20 including but not limited to, the interior or exterior wall surfaces of these components. In one embodiment, sensors can be encapsulated in the module 50 of ultraviolet light emitting sources 12.

One example of these sensors can include at least one fluorescent sensor (e.g., a fluorometer) to detect the fluorescence emissivity of the liquid after irradiation by one or more of the ultraviolet light emitting sources 12. Other sensors can include a temperature sensor to detect the temperature about the liquid chamber, a pressure sensor to detect the pressure of the liquid with respect to the liquid chamber, a humidity sensor to detect the humidity about the liquid chamber and/or the liquid collection reservoir, an ultraviolet radiation sensor to detect the ultraviolet intensity of the liquid, and a chemical sensor (e.g., a pH sensor, a chlorine sensor, an alkalinity sensor, a nitrate sensor, a salinity sensor, etc.) to detect chemical components in the liquid.

In one embodiment, a sensor can include a visible camera configured to obtain images from any of a number of various locations about the liquid in the liquid chamber 24 or the surface of an object placed in the chamber for irradiation. For example, the images can be used to compare images from these locations at different times in order to detect the presence of any contaminants.

The control unit 26 can obtain data from any of these sensors and use this data to control the irradiation of the liquid. In this manner, the ultraviolet light emitting sources 12, the control unit 26 and the sensors enable the various embodiments to incorporate a feedback mechanism that facilitates monitoring the irradiation of the liquid. For example, this feedback mechanism enables the control unit 26 to determine a presence of harmful contaminants about the liquid based on the conditions detected by the sensor(s). This allows the control unit 26 to direct the ultraviolet light emitting sources 12 to irradiate the liquid at locations where there is a presence of harmful contaminants for removal and suppression thereof.

In one embodiment, a fluorescent sensor can be utilized to detect a fluorescent response from the liquid in the liquid chamber 12 that is stimulated by the ultraviolet light emitting sources 12. To this extent, the fluorescent sensor can generate a fluorescent signal representative of the intensity of the fluorescence in the fluorescent response. The control unit 26 can then determine whether the intensity of a fluorescent signal detected by the fluorescent sensor is indicative of a contamination condition present in the liquid in the liquid chamber 24. In this manner, the control unit 26 can activate the ultraviolet light emitting sources 12 to perform a disinfection operation on the liquid in the liquid chamber in response to determining the contamination condition. In one scenario, the ultraviolet light emitting sources 12 can direct at least one of the blue ultraviolet light emitting sources 12A and/or the UV-C light emitting sources 12B to perform the disinfection operation depending on a level of extent of the contamination condition determined by the control unit. For example, the control unit 26 can direct the set of blue ultraviolet light emitting sources 12A to continuously radiate the liquid in the liquid chamber 24 for a predetermined prolonged period of time to inhibit biological growth and the set of UV-C light emitting sources 12B to radiate the liquid in a pulsed regime to reduce biological activity below a target level. For example, the time/duration of the UV-A exposure can range from ten minutes to tens of hours, while the time/duration of the UV-C exposure can be five minutes or less.

In another embodiment, the fluorescent sensor can be further configured to detect the intensity, the dosage, and the wavelength of the ultraviolet light that irradiates the liquid in the liquid chamber 24. The control unit 26 can be configured to determine whether the intensity of the fluorescent signal detected by the fluorescent sensor is indicative of a contamination condition present in the liquid, or on a surface of the liquid chamber 24 or of an object placed in the chamber for a treatment. In this manner, the control unit 26 can activate one or more of the ultraviolet light emitting sources 12 that are configured to operate as an UV-C light emitting source 12B and/or blue ultraviolet light emitting source 12A to perform a disinfection operation on the liquid or object in response to determining the contamination condition.

In one embodiment, the control unit 26 can operate in conjunction with an ultraviolet radiation sensor and a fluorescent sensor. For example, the ultraviolet radiation sensor can be configured to detect the ultraviolet intensity of the liquid in the liquid chamber 24 after being irradiated with ultraviolet radiation from a first ultraviolet light emitting source or set of sources, while the fluorescent sensor can be configured to detect the fluorescent illumination intensity of the liquid after being irradiated by a second ultraviolet light emitting source or set of sources. In this manner, the control unit 26 can receive signals indicative of the conditions detected by the ultraviolet radiation sensor and the fluorescent sensor, and determine a liquid transparency of the liquid and a density level of a particular contaminant. If the control unit 26 determines that the contaminant density level is too high (e.g., the contaminant density level satisfies a predetermined threshold), then it can activate the operation of the ultraviolet light emitting sources 12 to eradicate the particular contaminant.

It is understood that aforementioned examples of sensors that can be used with the liquid storage and dispensing device 62 of FIG. 3A as well as the other embodiments of the invention are illustrative of a few options that can be used in conjunction with the control unit 26 to control the irradiation of a liquid or an object placed in the liquid chamber with the ultraviolet light emitting sources 12, and are not meant to be limiting. Further, it is understood that this control of the irradiation includes the control unit 26 monitoring the irradiation by the ultraviolet light emitting sources 12 and adjusting of any of the previously mentioned irradiation parameters based on feedback conditions detected by the sensors.

The control unit 26 can include a number of different components that enable it to control the ultraviolet light emitting sources 12 and make determinations relating to the irradiation of the liquid or objects based on data obtained from the sensors. For example, in addition to the timer and user input/output component 36, the control unit 26 can include a memory storage that is capable of recording the various data obtained from the sensors. To this extent, the control unit 26 can retrieve the data for further analysis and optimization of the irradiation parameters of the ultraviolet light emitting sources 12.

The control unit 26 and/or the sensor(s) can include a wireless transmitter and receiver that is configured to facilitate communications with each other at a remote location via WiFi, BLUETOOTH, and/or the like. As used herein, a remote location is a location that is apart from any of the liquid storage and dispensing devices described herein. For example, a remote computer can be used to transmit operational instructions to the wireless transmitter and receiver. The operational instructions can be used to program functions performed and managed by the control unit 26 and the sensors. In another embodiment, the wireless transmitter and receiver can transmit ultraviolet treatment results, data from and to the remote computer, to facilitate maintenance and diagnostic operations on the liquid storage and dispensing devices.

The liquid storage and dispensing device of the various embodiments can be further configured with other components that complement the irradiation of the liquid in order to further enhance the sterilization, disinfection, cleaning and/or treatment. For example, FIG. 3A shows that the liquid storage and dispensing device 62 can include a liquid mixing element 68 to circulate liquid in the liquid chamber 24. Examples of a liquid mixing element can include, but are not limited to, stirrers with paddles, fluid circulation pumps, flow barriers, etc.

Figure 3B:
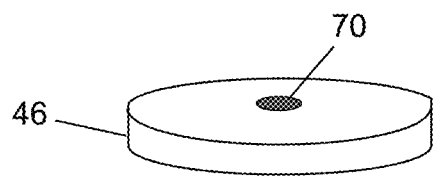
FIG. 3B shows a power station with an insertable electrical contact that is removably attachable with the bottom portion of the device for supplying power to the sources, sensors and mixing element according to an embodiment.

In one embodiment, the liquid mixing element 68 can be placed in the bottom region 30 of the liquid chamber 24 positioned about the module 50 of ultraviolet light emitting sources 12. As shown in FIGS. 3A and 3B, the liquid mixing element 68 can be removably attachable with an electrical insertable contact 70 that is associated with the power station 46. In operation, the liquid mixing element 68 can be controlled by the control unit 26 to operate in one of a variety of modes. In one embodiment, the control unit 26 can direct the liquid mixing element 68 to circulate the liquid in the liquid chamber 24 prior to, or during irradiation by the ultraviolet light emitting sources 12. To this extent, the control unit 26 can be configured to activate the liquid mixing element 68 during the irradiation of the liquid in the liquid chamber 24 with the plurality of ultraviolet light emitting sources 12, or prior to the irradiation. In one scenario, the control unit 26 can be configured to periodically activate the liquid mixing element 68 to provide periodic excitation of the liquid in the liquid chamber 24.

As mentioned herein, the liquid storage and dispensing devices of the various embodiments can be utilized to irradiate objects in the liquid chamber in instances when the chamber is unoccupied with liquid for purposes of sterilization, disinfection, cleaning and/or treatment. In this manner, the ultraviolet light emitting sources 12 can be used to remove harmful bacteria, viruses, germs, parasitic agents, micro-organisms, pathogens, contaminants, and the like from the object. It is understood, that only objects that are sized for placement within the liquid chamber 24 are suitable for such an embodiment. Examples of objects that can fit in a liquid chamber of a typical liquid storage and dispensing device (e.g., water pitcher or water container) can include, but are not limited to, utensils, toothbrushes, razors, brushes, containers, etc. All of these objects and other similarly sized objects that can be subject to harmful contaminants can be considered candidates for placement in the liquid chamber 24 for irradiation by the ultraviolet light emitting sources 12 in order to suppress, remove and eliminate such contaminants.

Figure 4A:
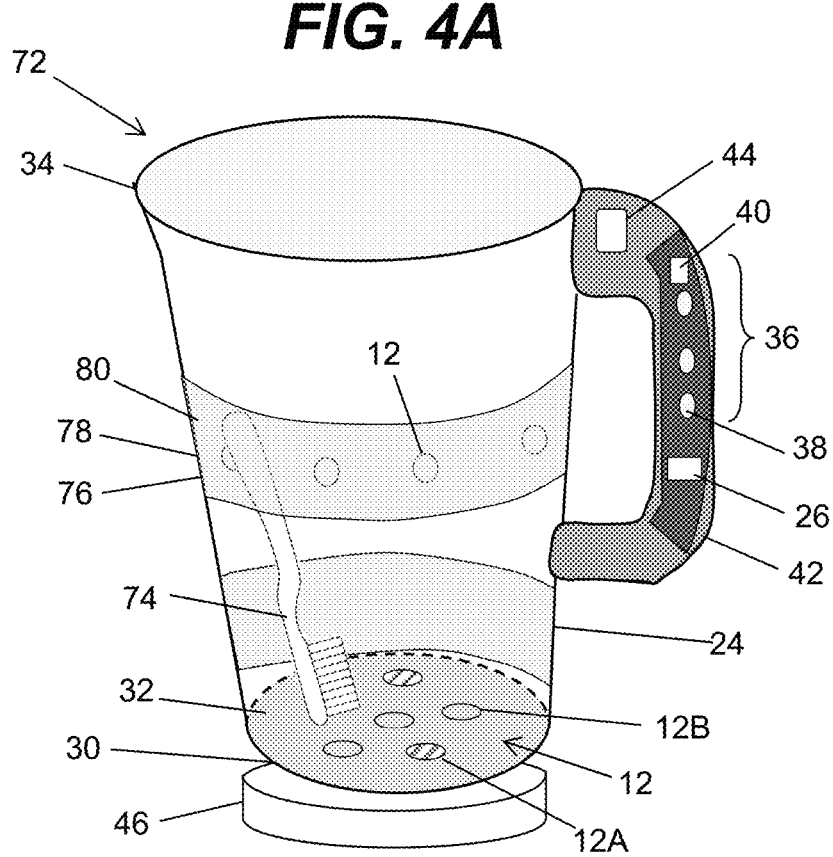
Figure 4B:
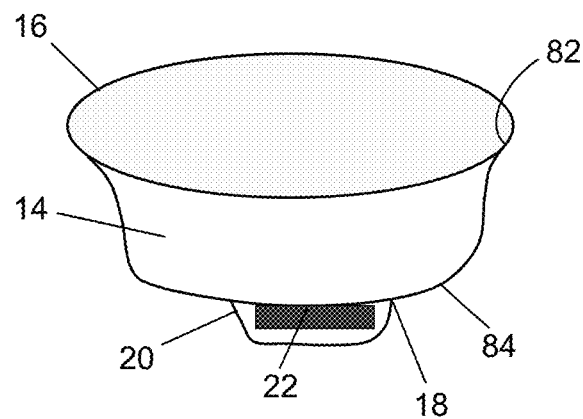
FIG. 4B shows a cover, a liquid collection reservoir and a filtering unit removed from the liquid chamber of the device depicted in FIG. 4A according to an embodiment.

FIGS. 4A-4B show a schematic of a liquid storage and dispensing device 72 with the cover 28 (not shown), the liquid collection reservoir 14 and the filtering unit 20 removed from the liquid chamber 24 (FIG. 4B) and an object 74 (e.g., a toothbrush) placed in the chamber (FIG. 4A). After the object 74 has been placed in the liquid chamber 24 and at least one of the cover 28, the liquid collection reservoir 14 and the filtering unit 20 is placed back over the liquid chamber, an irradiation treatment can then be initiated. For example, in one embodiment, a user can initiate the treatment by utilizing the user input/output component 36 to directly input any of the aforementioned irradiation parameters (e.g., dosage, duration, wavelength, etc.). Although not shown, it is understood that sensors can be deployed about the liquid chamber 24 to detect conditions associated with the irradiation, and the control unit 26 can utilize such conditions to control the irradiation of the object.

FIGS. 4A-4B further show that the liquid storage and dispensing device 72 can be implemented with other components that can enhance the irradiation of the object 74. In particular, FIG. 4A shows that the liquid storage and dispensing device 72 can include ultraviolet light emitting sources 12 in various locations about the liquid chamber 24. For example, in addition to having ultraviolet light emitting sources 12 located in the bottom region 30 of the liquid chamber 24, another set of sources 12 can be located on an inner wall surface 76 of the liquid chamber. The ultraviolet light emitting sources 12 can be located in a variety of positions about the inner wall surface 76 of the liquid chamber 24. The ultraviolet light emitting sources 12 can extend around the inner wall surface 76 at these positions or the sources can be positioned at specific regions around the inner wall surface. Further, the ultraviolet light emitting sources 12 can be oriented to emit the ultraviolet light emitting sources at a variety of directions and can be configured to emit the light at different intensities, dosage, wavelengths, patterns, duration, etc. Although FIG. 4A shows ultraviolet light emitting sources 12 positioned in the middle portion 78 of the liquid chamber 24, it is understood that the sources can be located anywhere about the liquid chamber including the exterior walls of the chamber.

In one embodiment, the set of ultraviolet light emitting sources 12 located on the inner wall surface 76 of the liquid chamber 24 can include blue ultraviolet light emitting sources configured to operate at a blue ultraviolet wavelength ranging from 360 nm to 460 nm, while the sources at the bottom region 30 can include UV-C light emitting sources configured to operate at a wavelength ranging from 260 nm to 290 nm. In this manner, the control unit 26 can direct the blue ultraviolet light emitting sources to continuously radiate the object 74 or liquid if in the liquid chamber 24 for a predetermined prolonged period of time to inhibit biological growth, and the UV-C light emitting sources to radiate the object or liquid in a pulsed regime to reduce biological activity below a target level. In a scenario, in which these sources are used to irradiate a liquid in the liquid chamber 24, the control unit 26 can be configured to control the intensity and a duration of the irradiation as a function of time that the liquid is stored in the liquid chamber and the amount of the liquid that is in the chamber.

A light guiding layer is another component that can be used with the liquid storage and dispensing devices of the various embodiments to enhance the irradiation of liquid or objects placed within the liquid chamber. As used herein, a light guiding layer means a transparent material that is configured to guide ultraviolet light therein for transmission at one or more predetermined locations. As shown in FIG. 4A, a light guiding layer 80 can be optically coupled to the set of ultraviolet light emitting sources 12 located on the inner wall surface 76 of the liquid chamber 24. To this extent, the ultraviolet light emitted from the ultraviolet light emitting sources 12 propagates through a region within the light guiding layer 80 before interacting with the liquid or objects in the liquid chamber 24. In one embodiment, the light guiding layer 80 can comprise one or more ultraviolet transparent layers. The one or more ultraviolet transparent layers can include at least one of roughness domains or diffusive domains that allow extraction of the ultraviolet light from the light guiding layer 80 to the liquid or object 74 in the liquid chamber 24. The one or more ultraviolet transparent layers can comprise glass. In one embodiment, the light guiding layer 80 can comprise scattering elements that interact with the light propagating through the light guiding layer and redirect the light in the liquid chamber 24. It is understood that the light guiding layer 80 can comprise other types of ultraviolet transparent wave guiding material including, but not limited to, an ultraviolet fiber, a diffusive ultraviolet emitter, and/or the like.

A reflective layer is another component that can be used with the liquid storage and dispensing devices of the various embodiments to enhance the irradiation of liquid or objects placed within the liquid chamber. In particular, the liquid storage and dispensing devices of the various embodiments can utilize a reflective layer to reflect the ultraviolet light generated from the ultraviolet light emitting sources 12. Having a reflective layer is beneficial in that it can facilitate and/or improve ultraviolet transmission, as well as promote recycling and light guiding of the radiation emitted from the sources 12. For example, in FIG. 4A, the inner wall surfaces 76 of the liquid chamber 24 can have at least one reflective layer to reflect the ultraviolet light generated from the ultraviolet light emitting sources 12 specularly or diffusively. The at least one reflective layer can include a fluoropolymer layer or an aluminum layer. In one embodiment, the at least one reflective layer can include UV-A or UV-C reflective material.

The reflective layer can include a number of different reflective materials. Examples of reflective material can include, but are not limited to, polished aluminum, PTFE (e.g., Teflon®), expanding polytetrafluoroethylene (ePTFE), ETFE or combinations thereof. In another embodiment, the reflective layer can include a diffusive ultraviolet reflective surface. The diffusive ultraviolet reflective surface can include a coating or thin film of a fluoropolymer. Examples of a fluoropolymer that are suitable as an ultraviolet reflective material that enables diffusive reflectivity can include, but are not limited to, expanding polytetrafluoroethylene (ePTFE) membrane (e.g., GORE® DRP® Diffuse Reflector Material), polytetrafluoroethylene (PTFE), and/or the like.

The reflective layer can also include a film or coating of ultraviolet reflective material applied to the inner wall surface 76 of the liquid chamber 24, an interior wall surface 82 or an exterior wall surface 84 of the liquid collection reservoir 14 (FIG. 4B). In general, a layer, film or coating of ultraviolet reflective material with a reflection coefficient of at least 50% will enable recycling of the ultraviolet radiation generated from the ultraviolet light emitting sources 12. Examples of ultraviolet reflective material that are suitable for use as a layer, film or coating can include, but are not limited to, polished aluminum, Bragg reflective dielectric mirrors, omni-directional mirrors comprising dielectric and metallic layers (e.g., aluminum), and/or the like. In one embodiment, the ultraviolet reflective material can include a diffusive ultraviolet reflective material such as a fluoropolymer. Examples of a fluoropolymer that is suitable as a diffusive ultraviolet reflective material that enables diffusive reflectivity can include, but are not limited to, expanding polytetrafluoroethylene (ePTFE) membrane (e.g., GORE® DRP® Diffuse Reflector Material), polytetrafluoroethylene (PTFE), and/or the like.

An optical element is another component that can be used with the liquid storage and dispensing devices of the various embodiments to enhance the irradiation of liquid or objects placed within the liquid chamber. In particular, the liquid storage and dispensing devices of the various embodiments can utilize one or more optical element to distribute the ultraviolet light emitted from the ultraviolet light emitting sources 12 about the liquid or object(s) in the liquid chamber 24. To this extent, the optical element can facilitate the irradiation of the liquid or the object(s) for purposes of sterilization, disinfection, cleaning and/or treating for eradicating harmful bacteria, viruses, germs, parasitic agents, micro-organisms, pathogens, contaminants and the like.

Examples of optical elements that are suitable for use with any of the liquid storage and dispensing devices of the various embodiments include, but are not limited to, a mirror, a reflector, a lens (e.g., a Fresnel lens and a total internal reflection (TIR)) lens, ultraviolet transparent wave guiding material, scattering elements, or a diffusive element. In one embodiment, a lens element formed from a fluoropolymer material that includes, but is not limited to, $SiO_2$, $CaF_2$, $MgF_2$, or a fluoropolymer can be located about the ultraviolet light emitting sources 12. In one embodiment, in which the ultraviolet light emitting sources 12 include blue UV light emitting sources and UV-C light emitting sources, the sources can have a diffusive layer positioned above the light emitting faces of the blue UV light emitting sources and/or the UV-C light emitting sources.

The aforementioned optical elements including the light guiding layer and the reflective layer can be arranged about the liquid storage and dispensing devices of the various embodiments in any of a number of configurations. For example, these optical elements can be disposed about the liquid collection reservoir 14, the liquid chamber 24 and the ultraviolet light emitting sources 12 in a number of locations that include, but are not limited to, on the inner wall surface 76 of the liquid chamber 24, on an external wall of the chamber, suspended within the chamber, about the interior and exterior surfaces 82 and 84 of the liquid collection reservoir 14. These optical elements can also be interspersed with the ultraviolet transparent material that may be used with any of these components.

Figure 5:
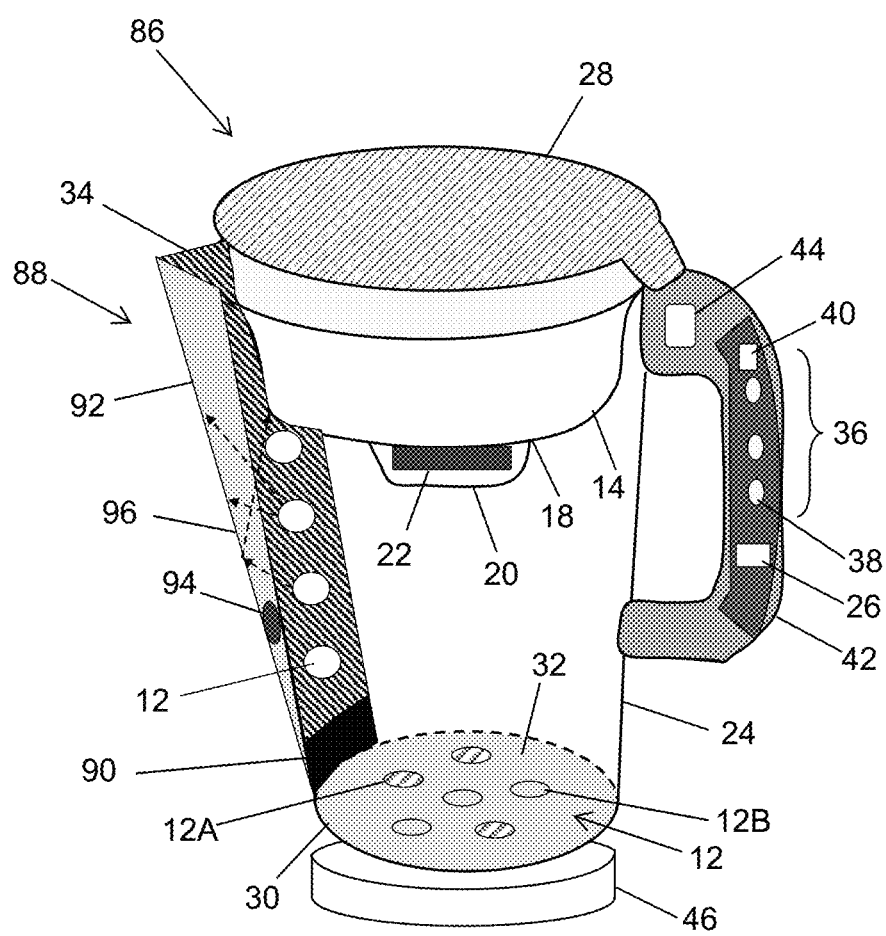
FIG. 5 shows a schematic of a liquid storage and dispensing device having ultraviolet light emitting sources in the bottom region of the device and in a liquid dispensing component of the device according to an embodiment.

As noted herein, the liquid storage and dispensing devices of the various embodiments can have the ultraviolet light emitting sources 12 located in a multitude of locations. FIG. 5 shows another example of a liquid storage and dispensing device having the ultraviolet light emitting sources 12 located in a multitude of locations. In particular, FIG. 5 shows a schematic of a liquid storage and dispensing device 86 having ultraviolet light emitting sources 12 in a liquid dispensing component 88 that is used to dispense liquid from the device. The ultraviolet light emitting sources 12 can complement the ultraviolet light emitting sources 12 located in the bottom region 30 of the liquid chamber 24 by further irradiating the treated liquid from the chamber with another dosage of ultraviolet light. The liquid dispenser component 88, which is fluidly coupled to the liquid chamber 24, can include a passage 90 that receives liquid from the liquid chamber, a pour spout 34 to facilitate pouring of the liquid from the liquid storage and dispensing device 86, and a channel 92 that carries liquid from the passage to the spout.

As shown in FIG. 5, the liquid dispenser component 88 can have a set of ultraviolet light emitting sources 12 located about the channel 92 to further irradiate the liquid flowing through the passage 90 from the liquid chamber 24 to the pour spout 34. In one embodiment, the set of ultraviolet light emitting sources 12 located about the channel 92 can comprise UV-C light emitting sources. To this extent, the UV-C light emitting sources can be used for a quick and final inactivation of bacteria and the like. It is understood that the intensity, duration and other irradiation parameters of the ultraviolet light emitting sources 12 about the liquid dispenser component 88 can be selected to predetermined levels that provide treatment of the liquid as it flows through the channel 92 and out the pour spout 34.

The set of ultraviolet light emitting sources 12 located about the channel 92 can be controlled by the control unit 26. For example, the control unit 26 can activate the ultraviolet light emitting sources 12 located about the channel 92 in response to data obtained by a sensor used with the liquid dispenser component 88. In one embodiment, as shown in FIG. 5, a tilt sensor 94 can be configured to detect an orientation angle or tilt in multiple axes of a reference plane from the channel 92 that is indicative of an angle that results in flow of liquid through the channel. Examples of a tilt sensor can include, but are not limited to, an inclinometer, tilt switches, etc. In one embodiment, the control unit 26 can activate the set of ultraviolet light emitting sources 12 located about the channel 92 in response to determining that the orientation angle detected by the tilt sensor exceeds a predetermined angle that is indicative of a position that liquid will flow from the liquid chamber and out of the liquid storage and dispensing device 86 via the pour spout 34. This allows the set of ultraviolet light emitting sources 12 located about the channel 92 to irradiate the liquid as the liquid flows from the passage 90 through the channel to the pour spout 34.

In one embodiment, the control unit 26 can periodically direct the set of ultraviolet light emitting sources 12 located about the channel 92 to irradiate inner surfaces 96 of the liquid dispenser component 88 in instances when liquid is not flowing therethrough for purposes of treating these surfaces. In one embodiment, the inner surfaces 96 of the liquid dispenser component 88 can have ultraviolet reflective material to recycle light within the channel 92 to further facilitate treating the surfaces and/or liquid that passes through the channel and out the pour spout 34. In one embodiment, portions of the inner surfaces 96 of the liquid dispenser component 88 can have regions that contain any of the aforementioned ultraviolet transparent material. To this extent, ultraviolet light generated from the ultraviolet light emitting sources 12 located about the channel 92 can irradiate the liquid in the liquid chamber 24 by transmission through these regions of ultraviolet transparent material. Similarly, the ultraviolet light generated from the ultraviolet light sources 12 in the bottom region 30 of the liquid chamber 24 can be used to irradiate the liquid flowing through the channel 92 to the pour spout 34. Also, in scenarios in which the liquid collection reservoir 14 contains regions that are transparent to ultraviolet radiation, the ultraviolet light emitting sources 12 can be used to irradiate this component. To this extent, the ultraviolet light emitting sources 12 can be used to contribute to the irradiation of multiple components of the liquid storage and dispensing device 86.

Figure 6A:
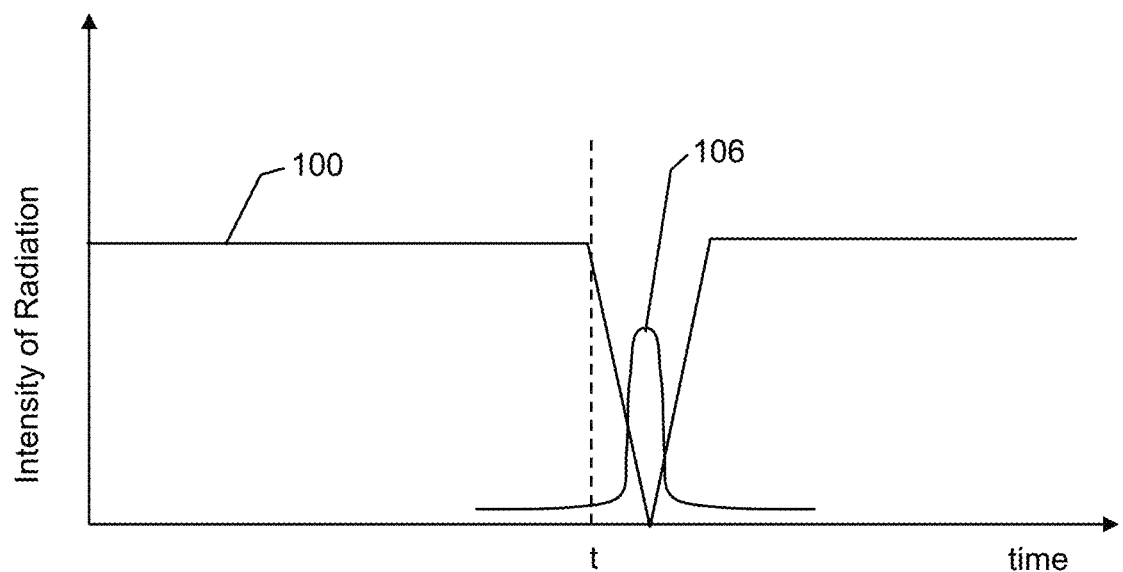
FIGS. 6A-6B show graphical examples depicting an ultraviolet irradiation treatment operation with a liquid storage and dispensing device according to an embodiment in which a first set of ultraviolet light emitting sources and a second set of ultraviolet light emitting sources are used to apply the ultraviolet irradiation treatment.
Figure 6B:
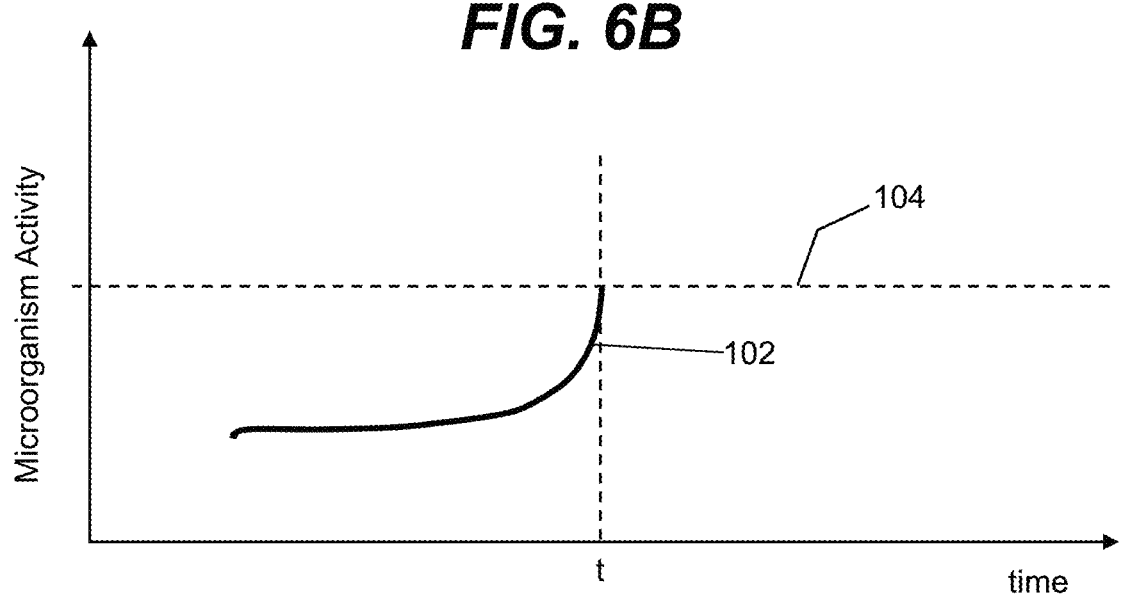

The liquid storage and dispensing devices of the various embodiments as described herein can be operated in a variety of manners to deliver an irradiation treatment to a body of fluid or an object. FIGS. 6A-6B show graphical examples depicting the operation of a liquid storage and dispensing device that utilizes a first set of ultraviolet light emitting sources and a second set of ultraviolet light emitting sources.

As shown in FIG. 6A, at section 100 of the graph, ultraviolet radiation from a set of light emitting sources that emit light such as blue-UV radiation can be used to determine whether there is any contamination in the fluid or on the object based on data from a sensor (e.g., an amplitude of a fluorescent signal sensed by a fluorescent sensor, visual data from a visual camera, and/or the like). For example, the object or the body of fluid can be irradiated with a light emitting source that is capable of eliciting a fluorescent signal if microbial activity is present. The amplitude of the fluorescent signal can indicate the level of contamination and/or the amount of microbial activity. The object or fluid can be irradiated by blue-UV radiation over a prolonged period of time that ranges from tens of minutes to tens of hours while determining whether there is a fluorescent signal. During this time, the control unit and the sensor (e.g., the fluorescence sensor, visual camera, and the like) can operate in conjunction to monitor the amount of contamination present on the surface of the object or in the fluid.

In this example, FIG. 6B shows a sharp increase in the growth of microorganism activity as noted by reference element 102. When the level of microorganism activity approaches a predetermined contamination threshold 104 at time t that is indicative of a need for more intense ultraviolet irradiation treatment due to rapid growth of microbial activity, then the control unit can direct a set of ultraviolet light emitting sources that can emit UV-C radiation to perform a more intense ultraviolet irradiation treatment at a short burst of intensity that lasts at most a few minutes (FIG. 6A, reference number 106) starting at or shortly after time t. In this manner, ultraviolet radiation (e.g., UV-C radiation) applied from the set of ultraviolet light sources that deliver UV-C radiation can bring microbial activity within appropriate limits by rapidly suppressing microbial activity on the surface of the object. The blue-UV radiation from the set of light emitting sources that generate this type of radiation can be used to maintain microbial activity within limits over an extended period of time, while the UV-C radiation from the ultraviolet light sources that deliver UV-C radiation can be used to rapidly suppress microbial activity.

It is understood that the liquid storage and dispensing devices of the various embodiments as described herein can include other components that can complement the irradiation of the liquid or objects in order to further enhance the sterilization, disinfection, treatment, and the like, of these items. For example, the liquid storage and dispensing devices can utilize other sources to irradiate the items such as at least one visible light emitting source that emits visible light to the liquid or object(s) in the liquid chamber. To this extent, the visible light emitting source(s) can aid the ultraviolet light emitting source(s) in disinfecting any harmful contaminants from the liquid or object(s) and suppressing further growth of these contaminants. Examples of visible light sources that can be used include, but are not limited to, visible light emitting diodes, fluorescent radiation sources, fluorescent lights, compact fluorescent lights, neon lights, incandescent lights, etc. In one embodiment, a set of blue and visible light emitting diodes can be used with the ultraviolet radiation sources.

In one embodiment, a photocatalyst material can be used with any of the various embodiments to facilitate the irradiation of liquid or objects placed in the liquid storage and dispensing devices, or even internal wall surfaces of the devices. For example, the photocatalyst material can undergo a photocatalytic reaction in response to being irradiated by ultraviolet radiation. This photocatalytic reaction can facilitate the removal and suppression of any harmful contaminants present on the surface of an object or a fluid being irradiated the ultraviolet light emitting source (s). The photocatalyst can include $TiO_2$, copper, silver and copper/silver particles, however, other photocatalysts such as, but not including, metal oxides, such as oxides of vanadium, chromium, titanium, zinc, tin, and cerium, can be used to enhance the sterilization and disinfection of the liquid or objects in a variety of applications.

In one embodiment, the photocatalyst can be irradiated by an ultraviolet wavelength in the presence of water vapor to result in formation of hydroxyl group radicals and reactive oxygen species (ROS) that can effectively interact and disrupt the proliferation of microorganisms. In an embodiment the ultraviolet wavelength can be in the range of 360 nm to 380 nm. In an alternative embodiment, the ultraviolet wavelength can be adjusted to be optimal for ROS and hydroxyl group radical formation for each type of photocatalyst used. It is understood that the photocatalyst should be positioned in proximity to the ultraviolet light to ensure that the created ROS and hydroxyl radicals can react with any harmful contaminants that may be present on the surface of object or in a body of fluid.

In one embodiment, an ultraviolet active photocatalyst can be placed on an inner wall surface of the liquid chamber 24. The ultraviolet active photocatalyst is configured to undergo a photocatalytic reaction in response to being irradiated by ultraviolet light generated from the ultraviolet light emitting sources 12 each operating at a peak wavelength. For example, the ultraviolet light emitting sources 12 can operate at a peak wavelength ranging 370 nm to 420 nm. To this extent, the photocatalytic reaction facilitates removal and suppression of any harmful contaminants present on the inner wall surfaces of the liquid chamber and/or in the liquid in the liquid chamber.

Figure 7:
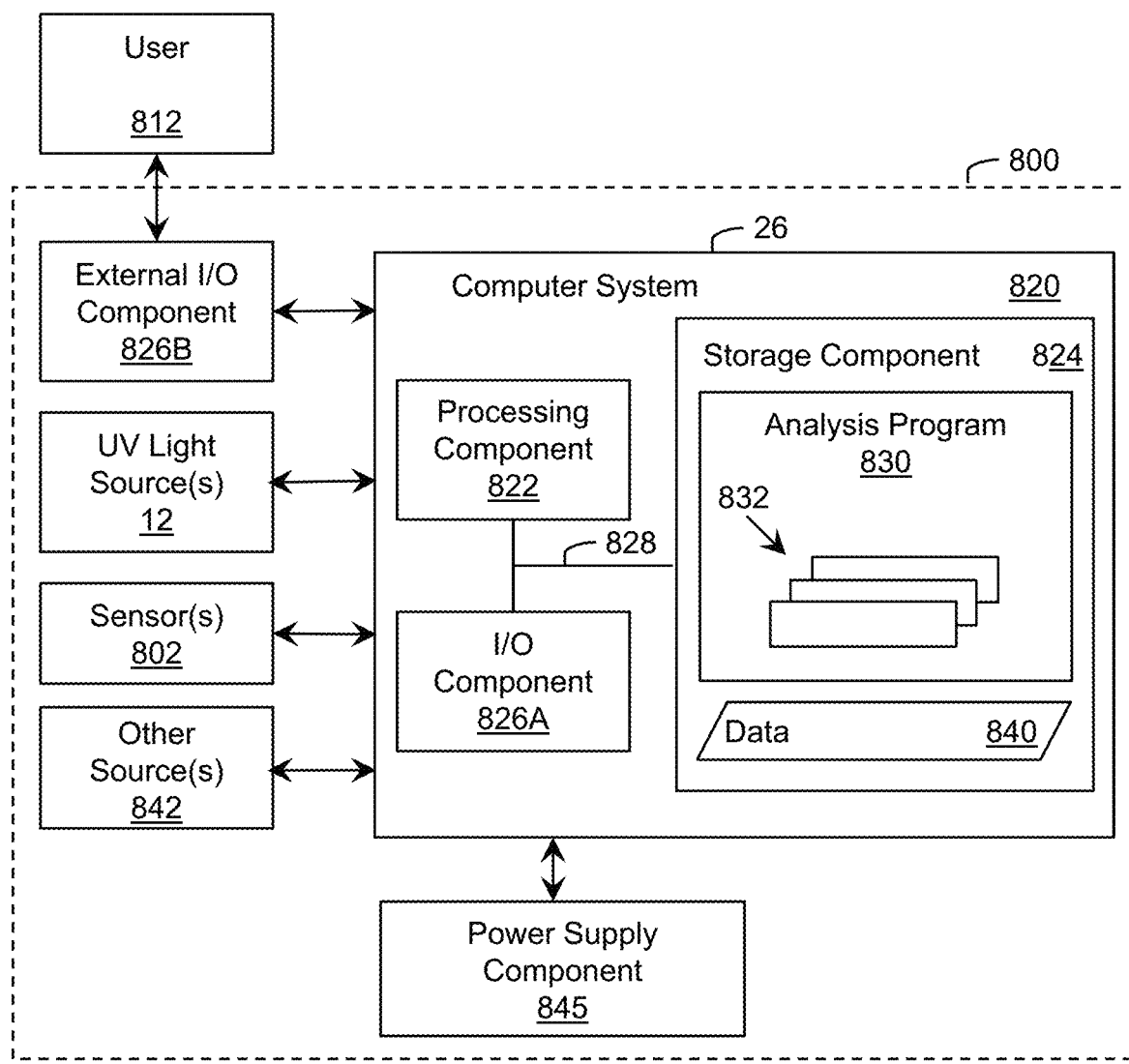
FIG. 7 shows a schematic block diagram representative of an overall processing architecture for irradiating liquid or an object that is applicable to any of the liquid storage and dispensing devices described herein according to an embodiment.

FIG. 7 shows a schematic block diagram representative of an overall processing architecture of a system 800 for irradiating liquid or an object that is applicable to any of the liquid storage and dispensing devices described herein according to an embodiment. In this embodiment, the architecture 800 is shown including the ultraviolet light emitting sources 12 and sensor(s) 802 for the purposes of illustrating the interaction of some of the components that can be used to provide an ultraviolet treatment.

As depicted in FIG. 7 and described herein, the system 800 can include a control unit 26. In one embodiment, the control unit 26 can be implemented as a computer system 820 including an analysis program 830, which makes the computer system 820 operable to manage the ultraviolet light emitting sources 12 and the sensor(s) 802 in the manner described herein. In particular, the analysis program 830 can enable the computer system 820 to operate the ultraviolet light emitting sources 12 to generate and deliver ultraviolet radiation and process data corresponding to one or more attributes regarding the irradiated item which can be acquired by the sensor(s) 802. The computer system 820 can individually control each ultraviolet light emitting source 12 and sensor 802 and/or control two or more of the ultraviolet light emitting sources and the sensors as a group. Furthermore, the ultraviolet light emitting sources 12 can emit ultraviolet radiation of substantially the same wavelength or of multiple distinct wavelengths, or at any other noted sets of peak wavelengths.

In an embodiment, during an initial period of operation, the computer system 820 can acquire data from at least one of the sensors 802 regarding one or more attributes of the item and generate data 840 for further processing. The data 840 can include information regarding a presence of biological activity (e.g., microorganisms, viruses, bacteria, and/or the like), an amount of radiation (e.g., ultraviolet, infrared, visible, and/or microwave) detected, and/or the like. The computer system 820 can use the data 840 to control one or more aspects of the ultraviolet radiation generated by the ultraviolet light emitting sources 12 during an ultraviolet treatment.

Furthermore, one or more aspects of the operation of the ultraviolet light emitting sources 12 can be controlled or adjusted by a user 812 via an external interface I/O component 826B. The external interface I/O component 826B can be located, for example, on the exterior of any of the aforementioned liquid storage and dispensing devices and used to allow the user 812 to selectively turn on/off the ultraviolet light emitting sources 12.

The external interface I/O component 826B can include, for example, a touch screen that can selectively display user interface controls, such as control dials, which can enable the user 812 to adjust one or more of: an intensity, scheduling, and/or other operational properties of the set of ultraviolet light emitting sources 12 or other sources (e.g., visible light emitting sources) 842 such as for example, operating parameters, radiation characteristics, and the like. In an embodiment, the external interface I/O component 826B could conceivably include a keyboard, a plurality of buttons, a joystick-like control mechanism, and/or the like, which can enable the user 812 to control one or more aspects of the operation of the set of ultraviolet light emitting sources 12. The external interface I/O component 826B also can include any combination of various output devices (e.g., an LED, a visual display), which can be operated by the computer system 820 to provide status information pertaining to a treatment for use by the user 812. For example, the external interface I/O component 826B can include one or more LEDs for emitting a visual light for the user 812, e.g., to indicate a status of the ultraviolet treatment. In an embodiment, the external interface I/O component 826B can include a speaker for providing an alarm (e.g., an auditory signal), e.g., for signaling that ultraviolet radiation is being generated or that an ultraviolet treatment has finished.

The computer system 820 is shown including a processing component 822 (e.g., one or more processors), a storage component 824 (e.g., a storage hierarchy), an input/output (I/O) component 826A (e.g., one or more I/O interfaces and/or devices), and a communications pathway 828. In general, the processing component 822 executes program code, such as the analysis program 830, which is at least partially fixed in the storage component 824. While executing program code, the processing component 822 can process data, which can result in reading and/or writing transformed data from/to the storage component 824 and/or the I/O component 826A for further processing. The pathway 828 provides a communications link between each of the components in the computer system 820. The I/O component 826A and/or the external interface I/O component 826B can comprise one or more human I/O devices, which enable a human user 812 to interact with the computer system 820 and/or one or more communications devices to enable a system user 812 to communicate with the computer system 820 using any type of communications link. To this extent, during execution by the computer system 820, the analysis program 830 can manage a set of interfaces (e.g., graphical user interface(s), application program interface, and/or the like) that enable human and/or system users 812 to interact with the analysis program 830. Furthermore, the analysis program 830 can manage (e.g., store, retrieve, create, manipulate, organize, present, etc.) the data, such as data 840, using any solution.

In any event, the computer system 820 can comprise one or more general purpose computing articles of manufacture (e.g., computing devices) capable of executing program code, such as the analysis program 830, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 830 can be embodied as any combination of system software and/or application software.

Furthermore, the analysis program 830 can be implemented using a set of modules 832. In this case, a module 832 can enable the computer system 820 to perform a set of tasks used by the analysis program 830, and can be separately developed and/or implemented apart from other portions of the analysis program 830. When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent monitoring and/or control systems that may perform a process described herein with regard to the control unit, the ultraviolet radiation sources and the sensors. To this extent, in other embodiments, the functionality provided by the computer system 820 and the analysis program 830 can be at least partially implemented by one or more computing devices that include any combination of general and/or specific purpose hardware with or without program code. In each embodiment, the hardware and program code, if included, can be created using standard engineering and programming techniques, respectively. In another embodiment, the control unit can be implemented without any computing device, e.g., using a closed loop circuit implementing a feedback control loop in which the outputs of one or more sensors are used as inputs to control the operation of a treatment. Illustrative aspects of the invention are further described in conjunction with the computer system 820. However, it is understood that the functionality described in conjunction therewith can be implemented by any type of monitoring and/or control system.

When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent computer systems that may perform a process described herein. To this extent, in other embodiments, the functionality provided by the computer system 820 and the analysis program 830 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 820 includes multiple computing devices, the computing devices can communicate over any type of communications link. Furthermore, while performing a process described herein, the computer system 820 can communicate with one or more other computer systems using any type of communications link. In either case, the communications link can comprise any combination of various types of wired and/or wireless links; any combination of one or more types of networks; and/or utilize any combination of various types of transmission techniques and protocols.

All of the components depicted in FIG. 7 can receive power from a power supply component 845. The power supply component 845 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power component can include solar, a mechanical energy to electrical energy converter such as a piezoelectric crystal, a rechargeable device, a power station, etc.

While shown and described herein as a system and method, it is understood that aspects of the present invention further provide various alternative embodiments. For example, in one embodiment, the various embodiments of the present invention can include a computer program fixed in at least one computer-readable medium, which when executed, enables a computer system to facilitate the ultraviolet irradiation treatment. To this extent, the computer-readable medium includes program code, such as the analysis program 830, which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; and/or the like.

In another embodiment, the present invention can provide a method of providing a copy of program code, such as the analysis program 830, which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the present invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the various embodiments of the present invention can implement a method that facilitates an ultraviolet irradiation treatment. This can include configuring a computer system, such as the computer system 820, to implement a method for facilitating the ultraviolet treatment. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A liquid storage and dispensing device, comprising:
   a liquid collection reservoir to receive an inflow of a liquid, the liquid collection reservoir having an inlet to receive the inflow of the liquid and an outlet to provide an outflow of the liquid;
   a filtering unit to filter the inflow of the liquid received by the liquid collection reservoir;
   a liquid chamber to store the liquid filtered by the filtering unit;
   a plurality of ultraviolet light emitting sources located on or sufficiently close to the liquid chamber to irradiate the liquid in the liquid chamber with ultraviolet light effective to treat the liquid;
   a set of sensors configured to determine an amount of time that the liquid is stored in the liquid chamber and an amount of the liquid that is in the liquid chamber; and
   a control unit, operatively coupled to the plurality of ultraviolet light emitting sources to control the irradiation of the liquid in the liquid chamber with the plurality of ultraviolet light emitting sources, wherein the control unit is configured to control an intensity and a duration of the irradiation as a function of the amount of time that the liquid is stored in the liquid chamber and the amount of the liquid that is in the liquid chamber.

2. The liquid storage and dispensing device of claim 1, wherein the plurality of ultraviolet light emitting sources comprise a set of ultraviolet light emitting sources placed about a bottom portion of the liquid chamber.

3. The liquid storage and dispensing device of claim 2, wherein the plurality of ultraviolet light emitting sources are removably attachable with the bottom portion of the liquid chamber.

4. The liquid storage and dispensing device of claim 3, further comprising an ultraviolet transparent window to separate the bottom portion of the liquid chamber from the plurality of ultraviolet light emitting sources.

5. The liquid storage and dispensing device of claim 1, wherein the plurality of ultraviolet light emitting sources comprise a set of ultraviolet light emitting sources located on an inner wall surface of the liquid chamber.

6. The liquid storage and dispensing device of claim 1, further comprising at least one optical element to distribute the ultraviolet light emitted from the plurality of ultraviolet light emitting sources about the liquid in the liquid chamber.

7. The liquid storage and dispensing device of claim 1, further comprising a fluorescent sensor configured to detect a fluorescent response from the liquid in the liquid chamber that is stimulated by the plurality of ultraviolet light emitting sources, and generate a fluorescent signal representative of an intensity of the fluorescent response, wherein the control unit is configured to determine whether the intensity of the fluorescent signal detected by the fluorescent sensor is indicative of a contamination condition present in the liquid in the liquid chamber, wherein the control unit is configured to activate the plurality of ultraviolet light emitting sources to perform a disinfection operation on the liquid in the liquid chamber in response to determining the contamination condition.

8. A liquid container, comprising:
   a liquid collection reservoir to receive an inflow of a liquid, the liquid collection reservoir having an inlet to receive the inflow of the liquid and an outlet to provide an outflow of the liquid;
   a filtering unit to filter the inflow of the liquid received by the liquid collection reservoir;
   a liquid chamber to store the liquid filtered by the filtering unit;
   a plurality of ultraviolet light emitting sources located on or sufficiently close to the liquid chamber to irradiate the liquid in the liquid chamber with ultraviolet light effective to treat the liquid, the plurality of ultraviolet light emitting sources including a set of blue ultraviolet light emitting sources configured to operate at a wavelength ranging from 360 nm to 460 nm and a set of ultraviolet-C (UV-C) light emitting sources configured to operate at a wavelength ranging from 260 nm to 290 nm;
   a set of sensors configured to determine an amount of time that the liquid is stored in the liquid chamber and an amount of the liquid that is in the liquid chamber; and
   a control unit, operatively coupled to the plurality of ultraviolet light emitting sources to control the irradiation of the liquid in the liquid chamber with the plurality of ultraviolet light emitting sources as a function of the amount of time that the liquid is stored in the liquid chamber and the amount of the liquid that is in the liquid chamber, wherein the control unit directs the set of blue ultraviolet light emitting sources to continuously irradiate the liquid in the liquid chamber for a predetermined prolonged period of time to inhibit biological growth and the set of UV-C light emitting sources to irradiate the liquid in a pulsed regime to reduce biological activity below a target level.

9. The liquid container of claim 8, wherein the set of sensors includes a fluorescent sensor configured to detect a fluorescent response from the liquid in the liquid chamber that is stimulated by the plurality of ultraviolet light emitting sources, and generate a fluorescent signal representative of an intensity of the fluorescent response, wherein the control unit is configured to determine whether the intensity of the fluorescent signal detected by the fluorescent sensor is indicative of a contamination condition present in the liquid in the liquid chamber, wherein the control unit is configured to activate the plurality of ultraviolet light emitting sources to perform a disinfection operation on the liquid in the liquid chamber in response to determining the contamination condition.

10. The liquid container of claim 8, wherein at least one sensor in the set of sensors comprises a liquid sensor that is configured to measure a liquid characteristic of the liquid in the liquid chamber, the liquid sensor comprising at least one of a liquid weight sensor that is configured to measure a weight of the liquid in the liquid chamber, a liquid level sensor that is configured to measure a level of the liquid in the liquid chamber, or a liquid transparency sensor that is configured to measure a transparency of the liquid in the liquid chamber.

11. The liquid container of claim 10, further comprising a timer that is operatively coupled with the liquid sensor, wherein the timer is configured to measure an amount of time that the liquid in the liquid chamber has the measured liquid characteristic, wherein the control unit is configured to activate the set of UV-C light emitting sources after the timer measures that the liquid has resided in the liquid chamber for a predetermined time duration.

12. A liquid pitcher, comprising:
a liquid collection reservoir to receive an inflow of a liquid, the liquid collection reservoir having an inlet to receive the inflow of the liquid and an outlet to provide an outflow of the liquid;
a filtering unit to filter the inflow of the liquid received by the liquid collection reservoir;
a liquid chamber to store the liquid filtered by the filtering unit;
a first set of ultraviolet light emitting sources located on or sufficiently close to the liquid chamber to irradiate the liquid in the liquid chamber with ultraviolet light effective to treat the liquid, the first set of ultraviolet light emitting sources including blue ultraviolet light emitting sources and ultraviolet-C (UV-C) light emitting sources;
a liquid dispenser component fluidly coupled to the liquid chamber that dispenses the liquid from the liquid chamber, the liquid dispenser component having a passage that receives the liquid from the liquid chamber, a pour spout to facilitate pouring of the liquid, a channel that carries the liquid from the passage to the pour spout, and a second set of ultraviolet light emitting sources comprising UV-C light emitting sources located on or sufficiently close to the channel to further irradiate the liquid flowing through the passage from the liquid chamber to the pour spout;
a set of sensors configured to determine an amount of time that the liquid is stored in the liquid chamber and an amount of the liquid that is in the liquid chamber; and
a control unit, operatively coupled to the first and second set of ultraviolet light emitting sources to control the irradiation of the liquid, wherein the control unit is configured to control an intensity and a duration of the irradiation as a function of the amount of time that the liquid is stored in the liquid chamber and the amount of the liquid that is in the liquid chamber; and
a user input/output component configured to facilitate user interaction with the control unit to control the irradiation of the liquid with at least one of the first set of ultraviolet light emitting sources or the second set of ultraviolet light emitting sources.

13. The liquid pitcher of claim 12, further comprising a light guiding layer optically coupled to at least one of the first set of ultraviolet light emitting sources or the second set of ultraviolet light emitting sources, wherein the ultraviolet light emitted from the first set of ultraviolet light emitting sources or the second set of ultraviolet light emitting sources propagates through a region within the light guiding layer before interacting with the liquid.

14. The liquid pitcher of claim 12, wherein at least one of the liquid collection reservoir, the liquid chamber, or the liquid dispenser component, comprises at least one region that is transparent to ultraviolet radiation.

15. The liquid pitcher of claim 14, wherein the at least one region that is transparent to ultraviolet radiation comprises at least one reflective layer to reflect the ultraviolet light.

16. The liquid pitcher of claim 12, wherein at least one sensor in the set of sensors is configured to detect operational conditions associated with the irradiation of the liquid.

17. The liquid pitcher of claim 16, wherein the control unit is configured to monitor the irradiation with the at least one sensor, and adjust irradiation parameters of the first set of ultraviolet light emitting sources and/or the second set of ultraviolet light emitting sources as a function of the operational conditions detected by the at least one sensor.

18. The liquid pitcher of claim 16, wherein the at least one sensor comprises a tilt sensor located on or sufficiently close to the liquid dispenser component, wherein the tilt sensor is configured to detect an orientation angle of the channel with respect to a reference plane, wherein the control unit is configured to active the second set of ultraviolet light emitting sources in response to determining that the orientation angle detected by the tilt sensor exceeds a predetermined angle.

19. The liquid storage and dispensing device of claim 1, further comprising a liquid dispenser component fluidly coupled to the liquid chamber that dispenses the liquid from the liquid chamber, the liquid dispenser component having a passage that receives the liquid from the liquid chamber, a pour spout to facilitate pouring of the liquid, a channel that carries the liquid from the passage to the pour spout, and a set of ultraviolet light emitting sources comprising ultraviolet-C (UV-C) light emitting sources located on or sufficiently close to the channel to further irradiate the liquid flowing through the passage from the liquid chamber to the pour spout.

20. The liquid storage and dispensing device of claim 19, further comprising a user input/output component configured to facilitate user interaction with the control unit to control the irradiation of the liquid with at least one of the plurality of ultraviolet light emitting sources located on or sufficiently close to the liquid chamber or the set of ultraviolet light emitting sources located on or sufficiently close to the channel.

* * * * *